(12) United States Patent
Bar-Or

(10) Patent No.: US 8,586,568 B2
(45) Date of Patent: Nov. 19, 2013

(54) METHODS AND PRODUCTS FOR TREATMENT OF DISEASES

(75) Inventor: David Bar-Or, Englewood, CO (US)

(73) Assignee: Ampio Pharmaceuticals, Inc., Greenwood Village, CO (US)

( * ) Notice: Subject to any disclaimer, the term of this patent is extended or adjusted under 35 U.S.C. 154(b) by 0 days.

(21) Appl. No.: 13/072,568

(22) Filed: Mar. 25, 2011

(65) Prior Publication Data

US 2011/0171307 A1 Jul. 14, 2011

Related U.S. Application Data

(62) Division of application No. 11/457,063, filed on Jul. 12, 2006.

(60) Provisional application No. 60/698,723, filed on Jul. 12, 2005, provisional application No. 60/711,157, filed on Aug. 24, 2005, provisional application No. 60/711,158, filed on Aug. 24, 2005.

(51) Int. Cl.
| | | |
|---|---|---|
| *A01N 45/00* | (2006.01) | |
| *A01N 43/80* | (2006.01) | |
| *A61K 31/56* | (2006.01) | |
| *A61K 31/58* | (2006.01) | |
| *A61K 31/42* | (2006.01) | |

(52) U.S. Cl.
USPC ........... 514/169; 514/172; 514/176; 514/177; 514/379

(58) Field of Classification Search
USPC .......................... 514/169, 172, 176, 177, 379
See application file for complete search history.

(56) References Cited

U.S. PATENT DOCUMENTS

| | | | |
|---|---|---|---|
| 3,135,743 A | | 6/1964 | Clinton et al. |
| 4,160,027 A | * | 7/1979 | Christiansen ............... 514/172 |
| 4,837,212 A | | 6/1989 | Harrington et al. |
| 4,975,537 A | | 12/1990 | Aristoff et al. |
| 4,994,443 A | | 2/1991 | Folkman et al. |
| 5,094,857 A | | 3/1992 | Luderschmidt |
| 5,372,996 A | | 12/1994 | Labrie |
| 5,407,926 A | | 4/1995 | Clark |
| 5,506,220 A | | 4/1996 | Schwadrohn |
| 5,620,921 A | | 4/1997 | Sullivan |
| 5,646,136 A | | 7/1997 | Petrow et al. |
| 5,679,666 A | | 10/1997 | Clark |
| 5,714,481 A | | 2/1998 | Schwartz et al. |
| 5,770,589 A | | 6/1998 | Billson et al. |
| 5,770,592 A | | 6/1998 | Clark |
| 5,929,111 A | | 7/1999 | Conrow et al. |
| 5,972,922 A | | 10/1999 | Wilks et al. |
| 5,990,099 A | | 11/1999 | Clark |
| 5,993,856 A | | 11/1999 | Ragavan et al. |
| 6,011,023 A | | 1/2000 | Clark et al. |
| 6,060,463 A | | 5/2000 | Freeman |
| 6,110,906 A | | 8/2000 | Labrie |
| 6,297,228 B1 | | 10/2001 | Clark |
| 6,333,317 B1 | | 12/2001 | Lee et al. |
| 6,413,540 B1 | | 7/2002 | Yaacobi |
| 6,562,369 B2 | | 5/2003 | Luo et al. |
| 6,610,674 B1 | | 8/2003 | Schreiber |
| 6,645,954 B2 | | 11/2003 | Carruthers |
| 6,663,865 B1 | | 12/2003 | Borrelli et al. |
| 6,936,599 B2 | | 8/2005 | Voskuhl |
| 2002/0055512 A1 | | 5/2002 | Marin et al. |
| 2003/0003144 A1 | | 1/2003 | Keller |
| 2003/0027772 A1 | | 2/2003 | Breton |
| 2003/0050291 A1 | | 3/2003 | Arad |
| 2003/0069232 A1 | | 4/2003 | Chiou |
| 2003/0232798 A1 | | 12/2003 | Arad |
| 2004/0063719 A1 | | 4/2004 | Adams et al. |
| 2004/0082557 A1 | | 4/2004 | Wajszczuk et al. |
| 2004/0137068 A1 | | 7/2004 | Bhushan |
| 2004/0138187 A1 | | 7/2004 | Reading et al. |
| 2004/0204392 A1 | | 10/2004 | Wood et al. |
| 2004/0219208 A1 | | 11/2004 | Kawamura et al. |
| 2005/0143362 A1 | | 6/2005 | McLane |
| 2005/0233965 A1 | | 10/2005 | Schwartz et al. |
| 2006/0233859 A1 | | 10/2006 | Whitcup et al. |
| 2007/0010494 A1 | | 1/2007 | Ehrhardt et al. |
| 2007/0111972 A1 | | 5/2007 | Bar-Or |
| 2007/0173538 A1 | | 7/2007 | Han et al. |
| 2008/0193499 A1 | | 8/2008 | Liu et al. |
| 2008/0214614 A1 | | 9/2008 | Lampe et al. |
| 2008/0249076 A1 | | 10/2008 | Holm et al. |
| 2008/0318875 A1 | | 12/2008 | Chibber |

(Continued)

FOREIGN PATENT DOCUMENTS

| | | |
|---|---|---|
| EP | 0244178 | 11/1987 |
| EP | 0501056 | 9/1992 |

(Continued)

OTHER PUBLICATIONS

Christiansen et al. 1984, J. Med. Chem, vol. 27, pp. 928-931.*
Anonymous "New program evaluates Modrenal in pre- and postmenopausal women," Thomson Reuters Drug News, Aug. 12, 2004, 1 page.
Dudas et al. "Protection against inflammatory neurodegeneration and glial cell death by 7 beta-hydroxy epiandrosterone, a novel neurosteroid," Neurobiol Dis, 2004, vol. 15, No. 2, pp. 262-268.
Hsiao et al. "Low-dose danazol in the treatment of livedoid vasculitis," Dermatology, Jan. 1997, vol. 194, No. 3, pp. 251-255.

(Continued)

*Primary Examiner* — Kara R McMillian
(74) *Attorney, Agent, or Firm* — Sheridan Ross P.C.

(57) ABSTRACT

The present invention relates to the treatment of diseases and conditions with an effective amount of a steroid having those formulas given in the specification, or a pharmacologically-acceptable salt or ester thereof. The disease or conditions treatable according to the invention include angiogenic diseases and conditions of the eye, angiogenic diseases and conditions of the brain, inflammatory diseases and conditions of the eye, inflammatory diseases and conditions of the brain and neurodegenerative diseases.

27 Claims, 4 Drawing Sheets

(56) References Cited

U.S. PATENT DOCUMENTS

| | | | |
|---|---|---|---|
| 2009/0105152 A1 | 4/2009 | Asami et al. |
| 2009/0312724 A1 | 12/2009 | Pipkin et al. |
| 2010/0323991 A1 | 12/2010 | Bar-Or |
| 2010/0324005 A1 | 12/2010 | Bar-Or |
| 2011/0171306 A1 | 7/2011 | Bar-Or |
| 2012/0035147 A1 | 2/2012 | Bar-Or |
| 2012/0077789 A1 | 3/2012 | Bar-Or |

FOREIGN PATENT DOCUMENTS

| | | |
|---|---|---|
| EP | 061943 | 8/1994 |
| EP | 0614463 | 9/1994 |
| EP | 0939124 | 9/1999 |
| EP | 1236469 | 9/2002 |
| EP | 1236470 | 9/2002 |
| EP | 1236471 | 9/2002 |
| EP | 1003553 | 8/2004 |
| GB | 1123770 | 8/1968 |
| GB | 2263109 | 7/1993 |
| GB | 2345851 | 7/2000 |
| JP | 01-301623 | 12/1989 |
| JP | 02-042020 | 2/1990 |
| JP | 04-149132 | 5/1992 |
| JP | 2003081875 | 3/2003 |
| WO | WO 86/02554 | 5/1986 |
| WO | WO 91/19731 | 12/1991 |
| WO | WO 93/10141 | 5/1993 |
| WO | WO 95/18621 | 7/1995 |
| WO | WO 00/02564 | 1/2000 |
| WO | WO 01/04349 | 1/2001 |
| WO | WO 01/30337 | 5/2001 |
| WO | WO 01/53321 | 7/2001 |
| WO | WO 01/68053 | 9/2001 |
| WO | WO 02/11676 | 2/2002 |
| WO | WO 02/069977 | 9/2002 |
| WO | WO 03/086178 | 10/2003 |
| WO | WO 2004/043480 | 5/2004 |
| WO | WO 2004/058289 | 7/2004 |
| WO | WO 2004/093852 | 11/2004 |
| WO | WO 2004/103406 | 12/2004 |
| WO | WO 2005/091853 | 10/2005 |
| WO | WO 2005/097121 | 10/2005 |
| WO | WO 2006/004795 | 1/2006 |
| WO | WO 2006/054119 | 5/2006 |
| WO | WO 2006/064291 | 6/2006 |
| WO | WO 2006/082588 | 8/2006 |
| WO | WO 2006/091459 | 8/2006 |
| WO | WO 2006/094027 | 9/2006 |
| WO | WO 2007/009087 | 1/2007 |
| WO | WO 2007/109363 | 9/2007 |
| WO | WO 2009/036108 | 3/2009 |
| WO | WO 2010/151530 | 12/2010 |

OTHER PUBLICATIONS

Matalliotakis et al. "The anti-inflammatory action of danazol and leuprorelin acetate depot on endometriosis is CRH independent," Inflammopharmacology, Jun. 2001, vol. 9, No. 3, pp. 249-255.
Surrey et al. "Direct effects of medroxyprogesterone acetate, danazol, and leuprolide acetate on endometrial stromal cell proliferation in vitro," Fertility and Serility, Aug. 1992, vol. 58, No. 2, pp. 273-278.
Wood "Microglia: A possible cellular target for pharmacological approaches to neurodegenerative disorders." Drug News and Perspectives, Apr. 1994, vol. 7, No. 3, pp. 138-157.
Partial Searh Report for European Patent Application No. 11010272. 0, dated Mar. 28, 2012 7 pages.
Partial Search Report for European Patent Application No. 11010269.6, dated Mar. 28, 2012 8 pages.
Extended Search Report for European Patent Application No. 11010270.4, dated May 11, 2012 4 pages.
Partial Search Report for European Patent Application No. 11010273.8, dated May 25, 2012 8 pages.
Extended Search Report for European Patent Application No. 11010271.2, dated May 29, 2012 6 pages.
"Danazol," http://www.drugs.com/pro/Danazol.html, copyright 2000-2010 (printed Dec. 10, 2010), 10 pages.
Adashi et al., "Direct biphasic effects of danazol on gonadotropin-dependent differentiation of cultured rat granulosa cells," Fertility and Sterility, Jun. 1986, vol. 45, No. 6, pp. 867-875.
Ahn et al., "Danazol for the treatment of idiopathic thrombocytopenic purpura," N Engl J Med, Jun. 1983, vol. 308(23), pp. 1396-1399 (Abstract Only).
Ahn et al., "Danazol therapy for autoimmune hemolytic anemia," Ann Intern Med, Mar. 1985, vol. 102(3), pp. 298-301 (Abstract Only).
Ahn et al., "Long-term danazol therapy in autoimmune thrombocytopenia: unmaintained remission and age-dependent response in women," Ann Intern Med, Nov. 1989, vol. 111(9), pp. 723-729 (Abstract Only).
Ahn et al., "Low-dose danazol therapy in idiopathic thrombocytopenic purpura," Annals of Internal Medicine, 1987, vol. 107, pp. 177-181.
Ahn, "Efficacy of danazol in hematologic disorders," Acta Haematol, 1990, vol. 84(3), pp. 122-129 (Abstract Only).
Akoum et al., "Secretion of interleukin-6 by human endometriotic cells and regulation by proinflammatory cytokines and sex steroids," Hum Reprod, Oct. 1996, vol. 11(1), pp. 2269-2275 (Abstract Only).
Al-Abdullah et al., "C1-inhibitor—biochemical properties and clinical applications," Crit Rev Immunol, 1985, vol. 5(4), pp. 317-330.
Aleksandrovskii, "Antithrombin III, C1 inhibitor, methylglyoxal, and polymorphonuclear leukocytes in the development of vascular complications in diabetes mellitus," Thromb Res, Jul. 1992, vol. 67(2), pp. 179-189 (Abstract Only).
Alessandrino et al., "Evidence- and consensus-based practice guidelines for the therapy of primary myelodysplastic syndromes. A statement from the Italian Society of Hematology," Haematologica, Dec. 2002, vol. 87, No. 12, pp. 1286-1306 (Abstract Only).
Alexopoulou, "Erectile dysfunction and lower androgenicity in type 1 diabetic patients," Diabetes Metab (Paris), 2001, vol. 27, 329-336.
Al-Momen et al., "Low-dose danazol for vascular access and dialyzer thrombosis in hemodialysis patients," Haemostasis, 1992, vol. 22(1), pp. 12-16 (Abstract Only).
Author Unknown, "Clinical Trial of Tamoxifen: University of Wisconsin, Madison," internet article, http://www.alsa.org/patient/drug.cfm?id=671, date unknown, printed Dec. 3, 2007.
Avina-Zubieta et al. "Long-term effectivemess of danazol corticosteroids and cytotoxic drugs in the treatment of hematologic manifestations of systemic lupus erythematosus," Lupus, 2003, vol. 12(1), pp. 52-57 (Abstract only).
Avvakumov et al., "Subcellular distribution and selectivity of the protein-binding component of the recognition system for sex-hormone-binding protein-estradiol complex in human decidual endometrium," Biochimica et Biophysica Acta, 1986, vol. 881, pp. 489-498.
Balash et al., "Acute pancreatitis associated with danazol treatment for endometriosis," Hum Reprod, Jun. 1994, vol. 9(6), pp. 1163-1165 (Abstract Only).
Banavali et al., "Danazol in treatment of angio-immunoblastic lymphadenopathy," Cancer, Aug. 1989, vol. 64(3), pp. 613-615 (Abstract Only).
Banks et al., "Release of the angiogenic cytokine vascular endothelial growth factor (VEGF) from platelets: significance for VEGF measuremnts and cancer biology," British Journal of Cancer, 1998, vol. 77(6), pp. 956-964.
Barbieri et al., "Comparison of the pharmacology of nafarelin and danazol," Am J Obstet Gynecol, Feb. 1990, vol. 162, pp. 581-585.
Barbieri et al., "Danazol: endocrine pharmacology and therapeutic applications," American Journal of Obstetrics and Gynecology, Oct. 15, 1981, vol. 141(4), pp. 453-463 (Abstract Only).
Barcz et al., "Serum VEGF (vascular endothelial growth factor) concentration in patients with endometriosis," Ginekol Pol, Sep. 2000, vol. 71(9), pp. 993-1000 (Abstract Only).
Bedrossian et al., "Diabetic retinopathy treated with testosterone," AMA Arch Ophthalmol, Sep. 1953, vol. 50, pp. 277-281.

(56) References Cited

OTHER PUBLICATIONS

Bell, "Danazol, Premenstrual Tension, and Uveitis," Arch Ophthalmol, 1989, vol. 107, pp. 796.

Birjmohun et al., "Effects of short-term and long-term danazol treatment on lipoproteins, coagulation, and progression of atherosclerosis: two clinical trials in healthy volunteers and patients with hereditary angioedema," Clinical Therapeutics, 2008, vol. 30(12), pp. 2314-2323.

Bishop et al., "The effect of danazol on tumour control and weight loss in patients on tamoxifen therapy for advanced breast cancer: a randomized double-blind placebo controlled trial," European Journal of Cancer, 1993, vol. 29A, No. 6, pp. 814-818 (Abstract Only).

Blanco et al., "Successful therapy with danazol in refractory autoimmune thrombocytopenia associated with rheumatic diseases," Br J Rheumatol, Oct. 1997, vol. 36(10), pp. 1095-1099 (Abstract Only).

Boucher et al., "Effect of hormonal agents on monocyte chemotactic protein-I expression by endometrial epithelial cells of women with endometriosis," Fertil Steril, Nov. 2000, vol. 74(5), pp. 969-975 (Abstract Only).

Braun et al., "Effect of danazol in vitro and in vivo on monocyte-mediated enhancement of endometrial cell proliferation in women with endometriosis," Fertility and Sterility, Jul. 1994, vol. 62, No. 1, pp. 89-95 (Abstract Only).

Bretza et al., "Hypertension: a complication of danazol therapy," Arch Intern Med, Oct. 1980, vol. 140(10), pp. 1379-1380 (Abstract Only).

Buttram, "Use of danazol in conservative surgery," J Reprod Med, Jan. 1990, vol. 35(1 Suppl), pp. 82-84 (Abstract Only).

Buzaid et al., "Management of myelodysplastic syndromes," Am. J. Med., Jun. 1986, vol. 80(6), pp. 1149-1157 (Abstract Only).

Carlstrom et al., "Peripheral levels of dehydroepiandrosterone sulfate, dehydroepiandrosterone, androstenedione, and testosterone following different doses of danazol," Acta Obstet Gynecol Scand Suppl, 1984, vol. 123, pp. 125-129.

Catalano, "Prolonged response to cyclosporin-A in hypoplastic refractory anemia and correlation with in vitro studies," Haematologica, 2000, vol. 85, pp. 133-138.

Cervera et al., "Danazol for systemic lupus erythematosus with refractory autoimmune thrombocytopenia or Evans' syndrome," J Rheumatol, Oct. 1995, vol. 22(10), pp. 1867-1871 (Abstract Only).

Chan et al., "Danazol therapy in autoimmune hemolytic anemia associated with systemic lupus erythematosus," J Rheumatol, Feb. 1991, vol. 18(2), pp. 280-282 (Abstract Only).

Chaurasia et al., "Sex hormones and diabetic retinopathy," Ann Ophthalmol, 1993, vol. 25, pp. 227-230.

Chevalier et al., "Danazol induced pancreatitis and hepatitis," Clin Rheumatol, Jun. 1990, vol. 9(2), pp. 239-241 (Abstract Only).

Colacurci et al., "Immune system and endometriosis," Acta Europaea Fertilitatis, May/Jun. 1991, vol. 22, No. 3, pp. 161-162 (Abstract Only).

Cole et al., "Danazol treatment of advanced prostate cancer: clinical and hormonal effects," The Prostate, 1986, vol. 9(1), pp. 15-20 (Abstract Only).

Connolly et al., "The effect of danazol in the MRL/lpr mouse model of autoimmune disease," Agents Actions, Aug. 1988, vol. 25(1-2), pp. 164-170 (Abstract Only).

Coombes et al., "Danazol Treatment for Advanced Breast Cancer," Cancer Chemotherapy and Pharmacology, 1983, vol. 10, pp. 194-195.

Coombes et al., "Danazol treatment of advanced breast cancer," Cancer Treatment Reports, Oct./Nov. 1980, vol. 63(10-11), pp. 1073-1076 (Abstract Only).

Damaj et al., "Remission of transformed myelodysplastic syndrome with fibrosis after danazol therapy," Eur J Haematol, Apr. 2002, vol. 68(4), pp. 233-235 (Abstract Only).

De Boer et al., "The Detection of Danazol and Its Significance in Doping Analysis," Journal of Analytical Toxicology, Jan./Feb. 1992, vol. 16, pp. 14-18.

De Oca Porto et al., "Gas chromatography/mass spectrometry characterization of urinary metabolites of danazol after oral administration in human," J. Chromatogr. B. Analyst. Technol. Biomed. Life Sci., Jan. 2006, vol. 830(1), pp. 178-183 (Abstract Only).

Diehl et al., "Autoimmune disease and chronic lymphocytic leukemia: autoimmune hemolytic anemia, oure red cell aplasia, and autoimmune thrombocytopenia," Seminars in Oncology, Feb. 1998, vol. 25(1), pp. 80-97 (Abstract Only).

Ding et al., "Sex differences of endogenous sex hormones and risk of type 2 diabetes: a systematic review and meta-analysis," JAMA, Mar. 15, 2006, vol. 295(11), pp. 1288-1299.

Dmowski, "Danazol. A synthetic steroid with diverse biologic effects," J Reprod Med, Jan. 1990, vol. 35 (1 Suppl), pp. 69-75.

Donaldson, "Danazol," The American Journal of Medicine, Sep. 1989, vol. 87, No. 3N, pp. 49N-55N (Abstract Only).

Drew et al., "Sex steroid regulation of microglial cell activation: relevance to multiple sclerosis," Ann NY Acad Sci, Dec. 2003, vol. 1007, pp. 329-334 (Abstract Only).

Du et al., "Administration of dehydroepiandrosterone suppresses experimental allergic encephalomyelitis in SJL/J mice," J Immunol, Dec. 2001, vol. 167(12); (Abstract Only).

El-Etr et al., "Steroid hormones in multiple sclerosis," J Neurol Sci, Jun. 2005, vol. 233(1-2), pp. 49-54 (Abstract Only).

El-Roeiy et al., "Danazol but not gonadotropin-releasing hormone agonists suppresses autoantibodies in endometriosis," Fertil Steril, Dec. 1988, vol. 50(6), pp. 864-871 (Abstract Only).

Fabiani et al., "Hereditary angioedema. Long-term follow-up of 88 patients. Experience of the Argentine Allergy and Immunology Institute," Allergol Immunopathol (Madr), Sep.-Oct. 2000, vol. 28(5), pp. 267-271 (Abstract Only).

Fabrykant et al., "Further Experience With Anabolic Steroids in Diabetic Retinopathy: Factors Precipitating Retinal Hemorrhages," Am J Med Sci, Sep. 1964, vol. 248, pp. 304-316.

Felinksi et al., "Glucocorticoid Regulation of Endothelial Cell Tight Junction Gene Expression: Novel Treatments for Diabetic Retinopathy," Current Eye Research, 2005, vol. 30, pp. 949-957.

Fenaux et al., "The role of danazol in the treatment of refractory idiopathic thrombocytopenic purpura. A report of 22 cases," Nouv Rev Fr Hematol, 1990, vol. 32(2), pp. 143-146 (Abstract Only).

Flynn, "Expression of Ia and the production of interleukin 1 by peritone exudates macrophages activated in vivo by steroids," Life Sciences, Jun. 30, 1986, vol. 38, No. 26, pp. 2455-2460 (Abstract Only).

Forbes et al., "Dosage-related effects of danazol on sex hormone binding globulin and free and total androgen levels," Clinical Endocrinology, 1986, vol. 25, pp. 597-605.

Ford et al., "Changes in haematological indices, blood viscosity and inhibitors of coagulation during treatment of endometriosis with danazol," Thromb Haemost, Aug. 1994, vol. 72(2), pp. 218-221 (Abstract Only).

Fraser et al., "Danazol treatment and platelet function," Med J Aust, Apr. 1980, vol. 1(7), pp. 313-314 (Abstract Only).

Freedman et al., "Treatment of prostatic carcinoma by gonadotropin inhibition with danazol: a preliminary report," Scandinavian journal of urology and nephrology. Supplementum, 1980, vol. 55, pp. 173-175 (Abstract Only).

Fujimoto et al., "Progestins and danazol effect on cell-to-cell adhesion, and E-cadherin and alpha- and beta-catenin mRNA expressions," J Steroid Biochem Mol Biol, Mar. 1996, vol. 57(5-6), pp. 275-282.

Fukui et al., "Association between serum testosterone concentration and collagen degradation fragments in men with type 2 diabetes mellitus," Metabolism Clinical and Experimental, 2007, vol. 56, pp. 1228-1232.

Fukui et al., "Low serum testosterone concentration in middle-aged men with type 2 diabetes," Endocrine Journal, 2007, vol. 54(6), pp. 871-877.

Gagne et al., "Levels of vascular endothelial growth factor (VEGF) in serum of patients with endometriosis," Human Reproduction, 2003, vol. 18(8), pp. 1674-1680.

Gao et al., "Extracellular carbonic anhydrase mediates hemorrhagic retinal and cerebral vascular permeability through prekallikrein activation," Nat Med, Feb. 2007, vol. 13(2), pp. 181-188 [Epub Jan. 28, 2007] (Abstract Only).

(56) References Cited

OTHER PUBLICATIONS

Geffray et al., "Efficacy of danazol in autoimmune hemolytic anemia with cold agglutinins. 4 cases," Presse Med, Sep. 1992, vol. 21(31), pp. 1472-1475 (Abstract Only).
Gelfand et al., "Treatment of hereditary angioedema with danazol. Reversal of clinical and biochemical abnormalities," The New England Journal of Medicine, Dec. 1976, vol. 295(26), pp. 1444-1448 (Abstract Only).
Graves et al., "Inflammation in amyotrophic lateral sclerosis spinal cord and brain is mediated by activated macrophages, mast cells and T cells," Amyotrophic Lateral Sclerosis, Dec. 2004, vol. 5(4), pp. 213-219 (Abstract Only).
Gurling, "Evaluation of an androgen, methylandrostenediol, in the treatment of diabetic retinopathy," Br J Ophthal, 1955, vol. 39, pp. 151-154.
Haffner et al., "Increased testosterone in type I diabetic subjects with severe retinopathy," Ophthalmology, Oct. 1990, vol. 97(10), pp. 1270-1274 (Abstract Only).
Hamed et al., "Pseudotumor cerebri induced by danazol," Am J Ophthalmol, Feb. 1989, vol. 107(2), pp. 105-110 (Abstract Only).
Han et al., "Approaches toward reversal of increased vascular permeability in C1 inhibitor deficient mice," Immunol Lett, Oct. 2003, vol. 89(2-3), pp. 155-160 (Abstract Only).
Haning et al., "Danazol and its principal metabolites interfere with binding of testosterone, cortisol, and thyroxin by plasma proteins," Clinical Chemistry, 1982, vol. 28, pp. 696-698 (Abstract Only).
Hardy et al., "Combination of Tamoxifen, Aminoglutethimide, Danazol and Medroxyprogesterone Acetate in Advanced Breast Cancer," European Journal of Cancer, 1990, vol. 26(7), pp. 824-827.
Harrison et al., "Maintenance therapy of cyclical mastalgia using low-dose danazol," J. R. Coll. Surg. Edinb., Apr. 1989, vol. 34, pp. 79-81.
Higa et al., "Autoimmune acquired form of angioedema that responded to danazol therapy," Intern Med, May 2002, vol. 41(5), pp. 398-402 (Abstract Only).
Higham et al., "A comparative study of danazol, a regimen of decreasing doses of danazol, and norethindrone in the treatment of objectively proven unexplained menorrhagia," American Journal of Obstetrics and Gynecology, Nov. 1993, vol. 169(5), pp. 1134-1139.
Hill et al., "Immunosuppressive effects of danazol in vitro," Fertility and Sterility, Sep. 1987, vol. 48, No. 3, pp. 414-418 (Abstract Only).
Holloway et al., "Prednisolone and danazol for treatment of immune-mediated anemia, thrombocytopenia, and ineffective erythroid regeneration in a dog," J Am Vet Med Assoc, Oct. 1990, vol. 197(8), pp. 1045-1048 (Abstract Only).
Hoots et al., "Aggressive combination therapy in the successful management of life-threatening intracranial hemorrhage in a patient with idiopathic thrombocytopenic purpura," Am J Pediatr Hematol Oncol, 1986, vol. 8(3), pp. 225-230 (Abstract Only).
Horstman et al., "Danazol Distribution in Plasma and Cell Membranes as Related to Altered Cell Properties: Implications for Mechanism," American Journal of Hematology, 1995, vol. 50, pp. 179-187.
Houstmuller et al., "Treatment of Diabetic Retinopathy With Anabolic Steroids," Netherl. Ophthal. Soc., 149th Meeting, Rotterdame 1962, Ophthamolgica, 1963, vol. 145, pp. 464-466.
Houstmuller et al., "Treatment of diabetic retinopathy with anabolic steroids," Ophthamologica, 1963, vol. 145, pp. 185-206.
Houstmuller, "The therapeutic applications of anabolic steroids in ophthalmology: biochemical results," Acta Endocrinol Suppl (Copenh), 1961, (Suppl 63), pp. 154-174.
Hsiao et al., "Low-dose danazol in the treatment of livedoid vasculitis," Dermatology, 1997, vol. 194(3), pp. 251-255 (Abstract only).
Hsieh et al., "Rhabdomyolysis and pancreatitis associated with coadministration of danazol 600 mg/d and lovastatin 40 mg/d," Clinical Therapeutics, 2008, vol. 30(7), pp. 1330-1335.
Hull et al., "Antiangiogenic Agents are Effective Inhibitors of Endometriosis," The Journal of Clinical Endocrinology & Metabolism, 2003, vol. 88(6), available at http://jcem.endojournals.org/cgi/content/full/88/6/2889, 20 pages.
Imai et al., "A gonadotropin-releasing hormone analogue impairs glucose tolerance in a diabetic patient," Eur J Obstet Gynecol Reprod Biol, 1998, vol. 76, pp. 121-122.
Jelkmann, "Pitfalls in the Measurement of Circulating Vascular Endothelial Growth Factor," Clinical Chemistry, 2001, vol. 47(4), pp. 617-623.
Jimenez et al., "Transendothelial migration of leukocytes is promoted by plasma from a subgroup of immune thrombocytopenic purpura patients with small-vessel ischemic brain disease," American Journal of Hematology, Mar. 2008, vol. 83(3), pp. 206-211.
Jolicoeur et al., "Comparative effect of danazol and a GnRH agonist on monocyto chemotactic protein-1 expression by endometriotic cells," Am J Reprod Immunol, Feb. 2001, vol. 45(2), pp. 86-93 (Abstract Only).
Jones et al., "Response of patients with amyotrophic lateral sclerosis to testosterone therapy: endocrine evaluation," Archives of Neurology, Nov. 1982, vol. 39, No. 11, pp. 721-722 (Abstract Only).
Kasamatsu et al., "A case of lung cancer with hereditary angioedema treated effectively by chemo-radiotherapy with C1 esterase inhibitor concentrate and danazol," Nihon Kokyuki Gakkai Zasshi, May 2004, vol. 42(5), pp. 435-439 (Abstract Only).
Kirk et al., "Angiogenesis in multiple sclerosis: is it good, bad or an epiphenomenon?" J Neurol Sci, Feb. 2004, vol. 217(2), pp. 125-130 (Abstract Only).
Kochakian et al., "Anabolic-Andorgenic Steroids: A Historical Perspective and Definition," Anabolic Steroids in Sport and Exercise, 2000, Second Edition, Chapter 1, pp. 17-49.
Konerding, "Delivery of antiangiogenic and antioxidant drugs of opthalmic interest through a nanoporous inorganic filter," Expert Opinion Therapeutic Targets, 2004, vol. 8(3), pp. 255-258.
Kosano et al., "Steroid-induced cataract: other than in the whole animal system in the lens culture system, androgens, estrogens and progestins as well as glucocotticoids produce a loss of transparency of the lens," Dev Ophthalmol, 2002, vol. 35, pp. 161-168 (Abstract Only).
Koumantakis et al., "Soluble serum interleukin-2 receptor, interleukin-6 and interleukin-1a in patients with endometriosis and in controls," Arch Gynecol Obstet, 1994, vol. 255(3), pp. 107-112 (Abstract Only).
Ledford et al., "Efficacy of Danazol in A Patient With Congenital Protein S Deficiency: Paradoxical Evidence for Decreased Platelet Activation With Increased Thrombin Generation," Thrombosis Research, Sep. 1997, vol. 87(5), pp. 473-482.
Liu et al., "Expression of vascular endothelial growth factor and endostatin in peritoneal fluid of patients with endometriosis," Di Yi Jun Yi Da Xue Xue Bao, Jan. 2004, vol. 24(1), pp. 69-71 (Abstract Only).
Lugassy et al., "Severe autoimmune hemolytic anemia with cold agglutinin and sclerodermic features—favorable response to danazol," Ann Hematol, Sep. 1993, vol. 67(3), pp. 143-144 (Abstract Only).
Maddox et al., "Low-dose danazol for mastalgia," The British Journal of Clinical Practice—Supplement, Nov. 1989, vol. 68, pp. 43-47.
Magri et al., "Comparative effect of the calcium antagonist verapamil and the synthetic steroids gestrinone and danazol on human monocyte phagocytosis in vitro," Gynecologic and Obstetric Investigation, 1997, vol. 43, No. 1, pp. 6-10 (Abstract Only).
Mahnke et al., "Vascular endothelial growth factor and interleukin-6 in peritoneal fluid of women with endometriosis," Fertil Steril, Jan. 2000, vol. 73(1), pp. 166-170 (Abstract Only).
Margolis et al., "Anabolic steroid preparations in the complex therapy of diabetic retinopathy (Russian)," Vestn Oftalmol, 1960, pp. 64-66 (Database Embase Abstract Only).
Marini et al., "Therapeutic efficacy of danazol in myelodysplastic syndromes," Eur J Cancer Clin Oncol, Sep. 1988, vol. 24(9), pp. 1481-1490 (Abstract Only).
Marwaha et al., "Danazol therapy in immune thrombocytopenic purpura," Petiatr Hematol Oncol, 1990, vol. 7(2), pp. 193-198 (Abstract Only).
Matalliotakis et al., "Changes in immunologic variables (TNF-a, sCD8 and sCD4) during danazol treatment in patients with endometriosis," Int J Fertil Womens Med, May-Jun. 1997, vol. 42(3), pp. 211-214 (Abstract Only).

(56) References Cited

OTHER PUBLICATIONS

Matalliotakis et al., "Serum concentrations of growth factors in women with and without endometriosis: the action of anti-endometriosis medicines," Int Immunopharmacol, Jan. 2003, vol. 3(1), pp. 81-89.
Matalliotakis et al., "The possible anti-inflammatory role of circulating human leukocyt antigen levels in women with endometriosis after treatment with danazol and leuprorelin acetate depot," Mediators Inflamm, Apr. 2001, vol. 10(2), pp. 75-80 (Abstract Only).
Meeks et al., "Danazol increases the anticoagulant effect of warfarin," Ann Pharmacother, May 1992, vol. 26(5), pp. 641-642 (Abstract Only).
Menon et al., "Evidence that danazol inhibits gonadotropin-induced ovarian steroidogenesis at a point distal to gonadotropin-receptor interaction and adenosine 3',5' cyclic monophosphate formation," Am. J. Obstet. Gynecol, Feb. 15, 1980, vol. 136(4), pp. 524-530.
Miyamura et al., "[Severe aplastic anemia remarkably improved by a treatment with antilymphocyte globulin, high-dose methylprednisolone and danazol]," Rinsho Ketsueki, Jan. 1989, vol. 30(1), pp. 72-77 (Abstract Only).
Mori et al., "Danazol suppresses the production of interleukin-1 beta and tumor necrosis factor by human monocytes," American Journal of Reproductive Immunology, Oct. 1990, vol. 24, No. 2, pp. 45-50 (Abstract Only).
Mosier et al., "Amyotrophic lateral sclerosis immunoglobulins increase Ca2+ currents in a motoneuron cell line," Annals of Neurology (only abstract has been provided), Jan. 1995, vol. 37, No. 1, pp. 102-109 (Abstract Only).
Mylvaganam et al., "Immune modulation by danazol in autoimmune thrombocytopenia," Clinical Immunology and Immunopathology, Mar. 1987, vol. 42, No. 3, pp. 281-287 (Abstract Only).
Mylvaganam et al., "Very low dose danazolin idiopathic thrombocytopenic purpura and its role as an immune modulator," Am J Med Sci, Oct. 1989, vol. 298(4), pp. 215-220 (Abstract Only).
Noel et al., "Myelodysplastic syndromes. Pathogenesis, diagnosis and treatment," Crit Rev Oncol Hematol, 1992, vol. 12(3), pp. 193-215 (Abstract Only).
Offner et al., "A synthetic androstene derivative and a natural androstene metaolite inhibit relapsing-remitting EAE," J Neuroimmunol, Sep. 2002, vol. 130(1-2), pp. 128-139 (Abstract Only).
Ota et al., "Effect of danazol on the immunocompetent cells in the eutopic endometrium in patients with endometriosis: a multicenter cooperative study," Fertil Steril, Mar. 1996, vol. 65(3), pp. 545-551 (Abstract Only).
Ota et al., "Effects of danazol at the immunologic level in patients with adenomyosis, with special reference to autoantibodies: a multicenter cooperative study," Am J Obstet Gynecol, Aug. 1992, vol. 167(2), pp. 481-486 (Abstract Only).
Pakhale et al., "Rapidly progressive pulmonary fibrosis in a patient treated with danazol for idiopathic thrombocytopenic purpura," Can Respir J, Jan.-Feb. 2004, vol. 11(1), pp. 55-57 (Abstract Only).
Petz, "Treatment of autoimmune hemolytic anemias," Curr Opin Hematol, Nov. 2001, vol. 8(6), pp. 411-416 (Abstract Only).
Pignon et al., "Danazol in autoimmune haemolytic anaemia," Br J Haematol, Feb. 1993, vol. 83(2), pp. 343-345 (Abstract Only).
Pitts et al., "Remissions induced in hereditary angioneurotic edema with an attenuated androgen (danazol): correlation between concentrations of C1-inhibitor and the forth and second components of complement," J Lab Clin Med, Oct. 1978, vol. 92(4), pp. 501-507 (Abstract Only).
Port et al., "Effects of a 3beta-hydroxysteroid dehydrogenase inhibitor on monocyte-macrophage infiltration into rat corpus luteum and on apoptosis: relationship to the luteolytic action of prolactin," J Reprod Fertil, May 2000, vol. 119(1), pp. 93-99 (Abstract Only).
Powles et al., "Clinical Trial of Multiple Endocrine Therapy for Metastatic and Locally Advanced Breast Cancer with Tamoxifen-Aminoglutethimide-Danazol Compared to Tamoxifen Used Alone," Cancer Research (Suppl.), Aug. 1982, vol. 42, pp. 3458s-3460s.
Prada et al., "Regulation of C1 inhibitor synthesis," Immunobiology, Aug. 1998, vol. 199(2), pp. 377-388 (Abstract Only).
Pride et al., "Relief of asthma in two patients receiving danazol for endometriosis," Can Med Assoc J, Oct. 1984, vol. 131(7), pp. 763-764 (Abstract Only).
Pronzato et al., "A Phase II Study with Danazol in Metastatic Breast Cancer," American Journal of Clinical Oncology, 1987, vol. 10, No. 5, pp. 407-409.
Proudler et al., "Insulin propeptides in conditions associated with insulin resistance in humans and their relevance to insulin measurements," Metabolism, Apr. 1994, vol. 43(4), pp. 446-449.
Roberts, "The History and Present Status of The Drug Development of Anabolic/Androgenic Steroids," available at http://www.mesomorphosis.com!articles/pharmacology|history-of-anabolic-steroids.htm, printed Dec. 29, 2009, publication date Jun. 1996, pp. 1-8.
Roselli et al., "The effect of anabolic-androgenic steroids on aromatase activity and androgen receptor binding in the rat preoptic area," Brain Res, May 1998, vol. 792(2), pp. 271-276 (Abstract Only).
Rosi et al., "Isolation, Synthesis, and Biological Activity of Five Metabolites of Danazol," Journal of Medicinal Chemistry, 1977, vol. 20(3), pp. 349-352.
Ruiz-Arguelles et al., "Protein S deficiency associated to anti-protein S antibodies in a patient with mixed connective-tissue disease and its reversal by danazol," Acta Haematol, 1993, vol. 89(4), pp. 206-208 (Abstract Only).
Ruiz-Irastorza et al., "Therapy of systemic lupus erythematosus: new agents and new evidence," Expert Opin Investig Drugs, Jul. 2000, vol. 9(7), pp. 1581-1593 (Abstract Only).
Sadek et al., "Prolonged complete remission of myelodysplastic syndrome treated with danazol, retinoic acid and low-dose prednisone," American Journal of Hematology, Aug. 2000, vol. 64(4), pp. 306-310 (Abstract Only).
Salek et al., "The influence of hormones and pharmaceutical agents on DHEA and DHEA-S concentrations: a review of clinical studies," J Clin Pharmacol, 2002, vol. 42, pp. 247-266.
Santaella et al., "Hereditary and acquired angioedema: experience with patients in Puerto Rico," P R Health Sci J, Mar. 2004, vol. 23(1), pp. 13-18 (Abstract Only).
Saskin et al., "Diabetic retinopathy. A new approach to therapy with a steroid hormone-testosterone propionate," Am J Ophthalmol, Apr. 1951, vol. 34(4), pp. 613-617.
Sato et al., "Comparative influence of steroid hormones and immunosuppressive agents on autoimmune expression in lacrim glands of a female mouse model of Sjogren's syndrome," Invest Ophthalmol Vis Sci, Apr. 1994, vol. 35(5), pp. 2632-2642 (Abstract Only).
Saulsbury et al., "Danazol therapy for chronic immune-mediated thrombocytopenic purpura in a patient with common variable immunodeficiency," Am j Pediatr Hematol Oncol, Fall 1991, vol. 13(3), pp. 326-329 (Abstract Only).
Schmaier et al., "Synthesis and expression of C1 inhibitor by human umbilical vein endothelial cells," The Journal of Biological Chemistry, Oct. 1989, vol. 264(30), pp. 18173-18179.
Schmidt et al., "Antioxidative and steroid systems in neurological and psychiatric disorders," The World Journal of Biological Psychiatry, 2005, vol. 6, pp. 26-35.
Schreiber et al., "Effect of danazol in immune thrombocytopenic purpura," N Engl J Med, Feb. 1987, vol. 316(9), pp. 503-508 (Abstract Only).
Schweppe et al., "[Effects of danazol therapy in endometriosis on the blood picture and blood coagulation]," Geburtshilfe Frauenheilkd, Sep. 1988, vol. 48(9), pp. 634-636 [Article in German] (Abstract Only).
Seifer et al., "Insulin-dependent diabetes mellitus associated with danazol," Am J Obstet Gynecol, Feb. 1990, vol. 162, pp. 474-475.
Seli et al., "Endometriosis: interaction of immune and endocrine systems," Semin Reprod Med, May 2003, vol. 21(2), pp. 135-144 (Abstract Only).
Shinmyozu et al., "[Occurrence of subdural hematoma closely associated with danazol administration in a patient with refractory ITP]," Rinsho Ketsueki, May 1990, vol. 31(5), pp. 674-675 [Article in Japanese] (Abstract Only).

(56) References Cited

OTHER PUBLICATIONS

Shinohara et al., "Idiopathic autoimmune hemolytic anemia successfully treated with danazol," Rinsho Ketsueki, Feb. 1990, vol. 31(2), pp. 256-257 (Abstract Only).
Singh et al., "Heterosteroids and drug research," Prog Med Chem, 1991, vol. 28, pp. 233-300.
Sullivan et al., "Androgen stimulation of lacrimal gland function in mouse mode of Sjogren's syndrome," J Steroid Biochem Mol Biol, Feb. 1997, vol. 60(3-4), pp. 237-245 (Abstract Only).
Sullivan et al., "Selectivity, specificity and kinetics of the androgen regulation of the ocular secretory immune system," Immunol Invest, May 1988, vol. 17(3), pp. 183-194 (Abstract Only).
Sur, "Experience with Danazol in the Treatment of Advanced Breast Cancer," Journal of the Indian Medical Association, Mar. 1989, vol. 87(3), pp. 71-72.
Szegedi et al., "Long-term danazol prophylaxis does not lead to increased carotid intima-media thickness in hereditary angioedema patients," Atherosclerosis, May 2008, vol. 198(1), pp. 184-191 [Epub Oct. 30, 2007] (Abstract Only).
Tainter et al., "Anabolic steroids in the management of the diabetic patient," New York State Journal of Medicine, Apr. 15, 1964, vol. 64, pp. 1001-1009.
Tan et al., "Danazol for treatment of refractory autoimmune hemolytic anaemia," Ann Acad med Singapore, Nov. 1989, vol. 18(6), pp. 707-709 (Abstract Only).
Thomas et al., "Effects of danazol on endothelial cell function and angiogenesis," Fertil Steril, Oct. 2007, vol. 88(4 Suppl), pp. 1065-1070 [Epub Mar. 23, 2007].
Tomino et al., "Clinical effect of danazol in patients with IgA nephropathy," Jpn J Med, May 1987, vol. 26(2), pp. 162-166.
Tomino et al., "Effect of danazol on solubilization of immune deposits in patients with IgA nephropathy," Am J Kidney Dis, Sep. 1984, vol. 4(2), pp. 135-140.
Tommassini et al., "Sex hormones modulate brain damage in multiple sclerosis: MRI evidence," J Neurol Neurosurg Psychiatry, Feb. 2005, vol. 76(2), pp. 272-275 (Abstract Only).
Tsang et al., "Effect of danazol on estradiol-17beta and progesterone secretion by porcine ovarian cells in vitro," Am. J. Obstet. Gynecol, Feb. 1979, vol. 133(3), pp. 256-259.
Valk, "Successes and Set-Backs in the Treatment of Diabetic Retinopathy With Anabolic Steroids During the Last Five Years," Netherl. Ophthal. Soc. 150th Meeting, Utrecht 1962, Ophthalmologica, 1963, vol. 146, pp. 325-350.
Van Vollenhoven et al., "Estrogen, progesterone, and testosterone: can they be used to treat autoimmune diseases?" Cleve Clin J Med, Jul.-Aug. 1994, vol. 61(4), pp. 276-284 (Abstract Only).
Vastag et al., "Endothelial cells cultured from human brain microvessels produce complement proteins factor H, factor B, C1 inhibitor, and C4," Immunobiology, Jul. 1998, vol. 199(1), pp. 5-13 (Abstract Only).
Vercellini et al., "Depot medroxyprogesterone acetate versus an oral contraceptive combined with very-low-dose danazol for long-term treatment of pelvic pain associated with endometriosis," Am J Obstet Gynecol, Aug. 1996, vol. 175(2), pp. 396-401.
Vercellini et al., "Very low dose danazol for relief of endometriosis-associated pelvic pain: a pilot study," Fertility and Sterility, Dec. 1994, vol. 62(6), pp. 1136-1142.
Vigano et al., "Danazol suppresses both spontaneous and activated human lymphocyte-mediated cytotoxicity," American Journal of Reproductive Immunology, Aug. 1992, vol. 28(1), pp. 38-42 (Abstract Only).
Vigano et al., "Immunosuppressive effect of danazol on lymphocyte-mediated cytotoxicity toward human endometrial stromal cells," Gynecological Endocrinology: The Official Journal of the International Society of Gynecological Endocrinology, Mar. 1994, vol. 8(1), pp. 13-19 (Abstract Only).
Watson et al., "Interactions between oestradiol and danazol on the growth of gastrointestinal tumour cells," Anticancer Research, Jan./Feb. 1993, vol. 13(1), pp. 97-102 (Abstract Only).
Webb et al., "Vascular endothelial growth factor (VEGF) is released from platelets during blood clotting: implications for measurement of circulating VEGF levels in clinical disease," Clin. Sci. (Lond), Apr. 1998, vol. 94(4), pp. 395-404 (Abstract Only).
Weiner, "Possible role of androgen receptors in amyotrophic lateral sclerosis: a hypothesis," Archives of Neurology, Mar. 1980, vol. 37(3), pp. 129-131 (Abstract Only).
Weinstock-Guttman et al., "What is new in the treatment of multiple sclerosis?" Drugs, Mar. 2000, vol. 59(3), pp. 401-410 (Abstract Only).
West et al., "Danazol for the treatment of refractory autoimmune thrombocytopenia in systemic lupus erythematosus," Ann Intern Med, May 1988, vol. 108(5), pp. 703-706 (Abstract Only).
Williams, "Metabolic effects of danazol," Am J Obstet Gynecol, Mar. 1991, vol. 164(3), pp. 933-934.
Wong, "Danazol in treatment of lupus thrombocytopenia," Asian Pac J Allergy Immunol, Dec. 1991, vol. 9(2), pp. 125-129 (Abstract Only).
International Search Report for International (PCT) Patent Application No. PCT/US06/27480, mailed May 17, 2007.
Written Opinion for International (PCT) Patent Application No. PCT/US06/27480, mailed May 17, 2007.
Extended European Search Report for European Patent Application No. 06787393.5, dated Sep. 28, 2009.
Official Action for European Application No. 06787393.5, dated Dec. 22, 2009.
Ambriz-Fernandez et al., "Danazol in refractory autoimmune thrombocytopenic purpura (ATP). A new therapeutic sequence," Arch Invest Med (Mex), Jul.-Sep. 1985, vol. 16(3), pp. 294-304.
Flores et al., "Danazol therapy in chronic immune thrombocytopenic purpura," Eur J. Haematol, Aug. 1990, vol. 45(2), pp. 109-110.
Grange et al., "Fatal acute pulmonary fibrosis in a patient treated by danazol from thrombocytopenia," Am J Hematol, Oct. 1996, vol. 53(2), p. 149.
Manoharan, "Danazol therapy in patients with immune cytopenias," Aust N Z J Med, Dec. 1987, vol. 17(6), pp. 613-614.
Rigau et al., "[Danazol in autoimmune hemolytic anemias: an alternative treatment]," Med Clin (Barc), Mar. 1986, vol. 86(8), 349-350.
Bork et al., "Benefits and risks of danazol in hereditary angioedema: a long-term survey of 118 patients," Allergy Asthma Immunol, 2008, vol. 100(2), pp. 152-161.
Bretza et al., "Hypertension: a complication of danazol therapy," Arch Intern Med, Oct. 1980, vol. 140(10), pp. 1379-1380.
Crook et al., "Lipoprotein Lp(a) levels are reduced by danazol, an anabolic steroid," Atherosclerosis, 1992, vol. 92(1), pp. 41-47.
Hopfl et al., "Long-term danazol therapy for hereditary angioedema," DMW (Deutsche Medizinische Wochenschrift), 1990, vol. 115(4), pp. 133-138 (includes English translation).
"Glomerular Diseases," NIDDK, Apr. 2006, NIH Publication No. 06-4358, 12 pages.
Clermont et al. "Role of the angiotensin II type 1 receptor in the pathogenesis of diabetic retinopathy: effects of blood pressure control and beyond," Journal of Hypertension, Mar. 2006, vol. 24, (suppl 1), pp. S73-S80.
Goh et al. "Agents in development for the treatment of diabetic nephropathy," Expert Opinion Emerging Drugs, Sep. 2008, vol. 13, No. 3, pp. 447-463.
Henz et al. "Treatment of physical urticaria: Antihistamines and alternative approaches," Allergologie, Dustri Verlag, Muenchen-Deisenhofen, DE, Jan. 2001, vol. 24, No. 2, pp. 56-65 (English Abstract).
Mansour et al. "The beneficial interaction between enalapriil and danazol in normal rat," Scientia Pharmaceutica, Oesterreichische Apotheker-Verlagsgesellschaft Mbh, Austria, Jun. 2002, vol. 70, No. 2, pp. 165-175.
Ng et al., "Targeting angiogenesis, the underlying disorder in neovascular age-related macular degeneration," Can. J. Ophthalmol., 2005, vol. 40(3), pp. 352-368 (Abstract only), 1 page.
U.S. Appl. No. 13/607,210, filed Sep. 7, 2012, Bar-Or.
Oda et al. "Hereditary angioneurotic edema (HANE): Report of a case," Jibi Inkoka Tokeibu Geka, Feb. 1999, vol. 71, No. 2, pp. 97-101 (English Abstract).

(56) References Cited

OTHER PUBLICATIONS

Extended Search Report for European Patent Application No. 11010272.0, dated Jul. 13, 2012 10 pages.
Extended Search Report for European Patent Application No. 11010269.0, dated Jul. 13, 2012 9 pages.
Davis et al., "Improvement of recurrent diabetic ketoacidosis due to danazol," Practical Diabetes, Nov./Dec. 1988, vol. 5, No. 6, p. 251.
Fujimoto, "Endocrinological Contribution for Invasion and Metastasis in Gynecological Cancers," (with English Synopsis) Acta Obstetrica et Gynaecologica Japonica, 1996, vol. 48, No. 8, pp. 633-643.
Fujimoto et al., "Antiestrogenic Compounds Inhibit Estrogen-Induced Expressions of Basic Fibroblast Growth Factor and Its mRNA in Well-Differentiated Endometrial Cancer Cells," General Pharmacology, 1997, vol. 28, Iss. 2, pp. 215-219.
Garcia-Velasco et al., "Medical treatment of endometriosis," Minerva Ginecologica, 2005, vol. 57, No. 3, pp. 249-255 (Abstract Only).
Kameda et al., "A Case of Chronic Lymphocytic Leukemia Complicated with Autoimmune Hemolytic Anemia Which was Successfully Treated by COP Combination Chemotherapy and Prednisolone and Subsequently by Danazol," (English Translation), Journal of Yamaguchi University Medical Association, 1997, vol. 46, No. 4, pp. 245-251.

* cited by examiner

Figure 3
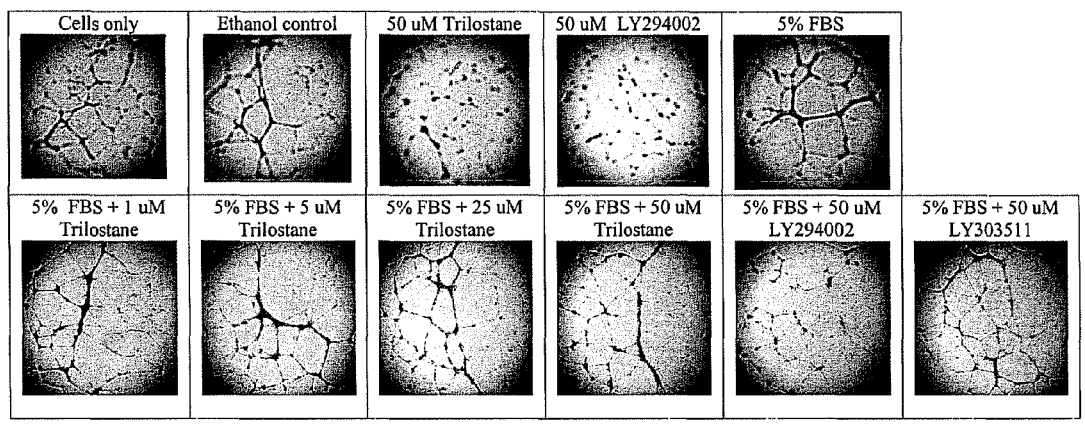
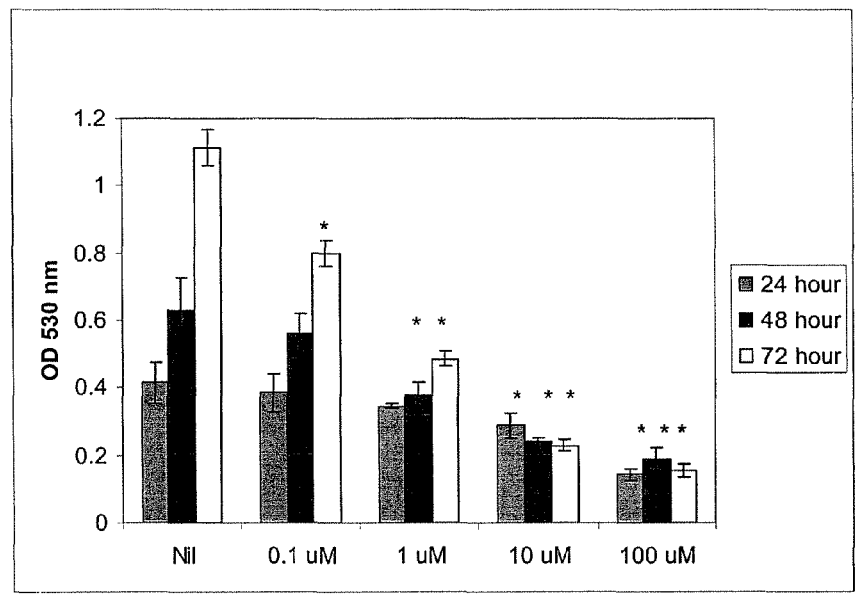
FIGURE 4

METHODS AND PRODUCTS FOR TREATMENT OF DISEASES

REFERENCE TO RELATED APPLICATIONS

This application is a divisional application of U.S. patent application Ser. No. 11/457,063 filed Jul. 12, 2006, which claims the benefit of provisional application No. 60/698,723, filed Jul. 12, 2005, provisional application No. 60/771,157, filed Aug. 24, 2005, and provisional application 60/711,158, filed Aug. 24, 2005. The disclosures of all of the foregoing provisional applications are incorporated herein in their entireties.

FIELD OF THE INVENTION

The present invention relates to the treatment of diseases and conditions with an effective amount of a steroid having those formulas given below, or a pharmacologically-acceptable salt or ester thereof. The disease or conditions treatable according to the invention include angiogenic diseases and conditions of the eye or brain, inflammatory diseases and conditions of the eye or brain, and neurodegenerative diseases.

BACKGROUND

Over time, diabetes affects the circulatory system of the retina causing diabetic retinopathy, which occurs in about forty percent of diabetics. The earliest phase of this disease is known as background diabetic retinopathy. The next stage is known as proliferative diabetic retinopathy. In this stage, circulation problems cause areas of the retina to become oxygen-deprived or ischemic. New, fragile vessels develop as the circulatory system attempts to maintain adequate oxygen levels within the retina. Unfortunately, these delicate vessels hemorrhage easily, and blood may leak into the retina and vitreous, causing spots or floaters, along with decreased vision. In the later phases of the disease, continued abnormal vessel growth and scar tissue may cause serious problems, such as retinal detachment and glaucoma. There are several treatments for diabetic retinopathy, depending on the stage of the disease and the specific problem that requires attention. However, there still remains a need for additional treatments, especially for one that is simple to administer and which has few side effects.

Age-related macular degeneration is the leading cause of severe vision loss in people age sixty and older. There are two forms of this disease—the dry form and the wet form. The wet form accounts for only about fifteen percent of all cases, but it is responsible for most of the severe vision loss that occurs in people suffering from macular degeneration. The abnormal growth of new blood vessels (called choroidal neovascularizations) is the cause of the severe vision loss that occurs in wet macular degeneration. There is a dire need for an effective treatment for wet macular degeneration, especially for one that is simple to administer and which has few side effects.

There is also clearly a need for additional and more effective treatments for brain tumors. Therapies that are effective for other tumors currently have serious limitations as brain tumor treatments. The blood brain barrier may create a particular obstacle to the effective use of chemotherapy in the treatment of brain tumors.

Many treatments have been proposed for neurodegenerative diseases or conditions. However, most of these treatments have not been successful, and there remains a need for additional treatments for these diseases.

SUMMARY OF THE INVENTION

The invention provides a method of treating an angiogenic disease or condition of the eye. The method comprises administering to an animal in need thereof an effective amount of a steroid of formula I or IV or a pharmacologically-acceptable salt or ester thereof.

The invention also provides a method of treating an inflammatory disease or condition of the eye. The method comprises administering to an animal in need thereof an effective amount of a steroid of formula I, IV or V or a pharmacologically-acceptable salt or ester thereof.

The invention further provides a pharmaceutical product suitable for treatment of the eye. The product comprises a steroid of formula I, IV or V or a pharmacologically-acceptable salt or ester thereof. Treatment of the eye avoids systemic side effects. Particularly preferred are topical pharmaceutical compositions because they are simple to administer to the eye.

The invention further provides a method of treating an angiogenic disease or condition of the brain. The method comprises administering to an animal in need thereof an effective amount of a steroid of formula I or IV or a pharmacologically-acceptable salt or ester thereof.

The invention also provides a method of treating an inflammatory disease or condition of the brain. The method comprises administering to an animal in need thereof an effective amount of a steroid of formula I, IV or V or a pharmacologically-acceptable salt or ester thereof.

The invention further provides a method of treating a neurodegenerative disease or condition of the brain. The method comprises administering to an animal in need thereof an effective amount of a steroid of formula I, IV or V or a pharmacologically-acceptable salt or ester thereof.

BRIEF DESCRIPTION OF THE DRAWINGS

FIG. 3 shows photographs of HUVEC cells taken after incubation with trilostane III as a measure of its ability to prevent tube formation of endothelial cells.

FIG. 4 shows the OD levels measured after incubation of HUVEC cells with danazol as a measure of its ability to prevent initial proliferation of endothelial cells.

DETAILED DESCRIPTION OF THE PRESENTLY-PREFERRED EMBODIMENTS OF THE INVENTION

Figure 1:
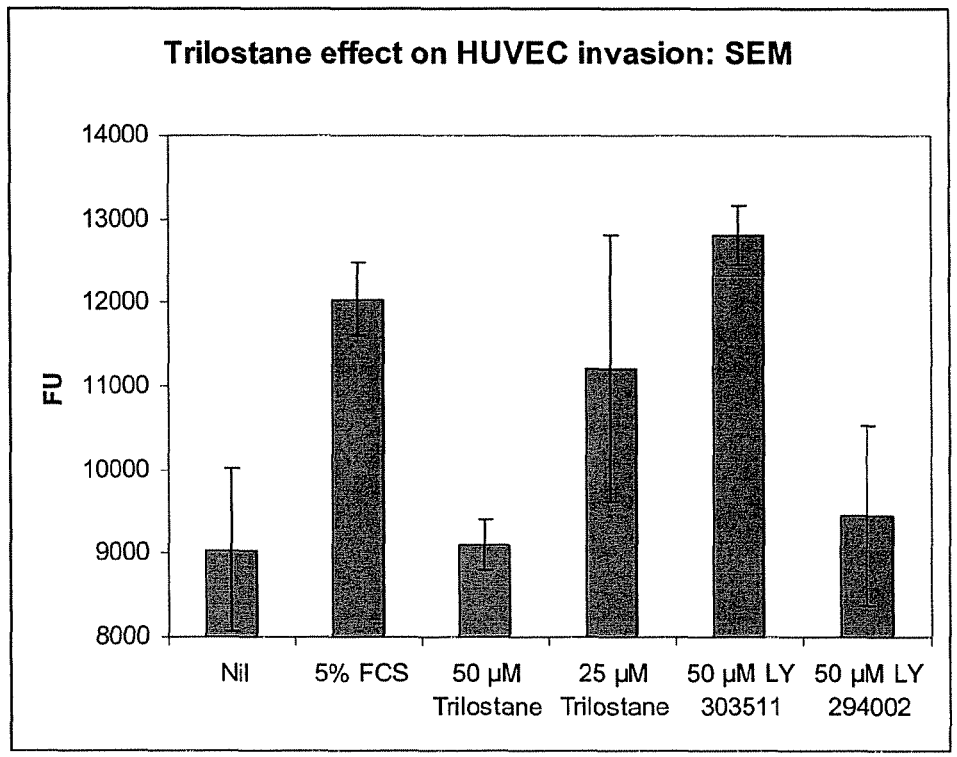
FIG. 1 shows the fluorescence measured after treatment of HUVEC cells with trilostane III as a measure of their ability to prevent endothelial cell invasion.

The invention provides a method of treating an angiogenic disease or condition of the eye. An "angiogenic disease or condition of the eye" is a disease or condition of the eye involving, exacerbated by, or caused by, angiogenesis. The method comprises administering to an animal in need thereof an amount of a steroid of formula I or IV or a pharmacologically-acceptable salt or ester thereof that is effective to inhibit the angiogenesis that is occurring in the eye.

Angiogenic diseases and conditions of the eye that can be treated according to the present invention include, but are not limited to, macular degeneration, diabetic retinopathy, neovascular glaucoma, retinopathy of prematurity, sickle-cell retinopathy, oxygen-induced retinopathy, neovascularization due to ocular insults (such as traumatic or surgical injury or transplantation of eye tissue) and tumors.

The invention also provides a method of treating an angiogenic disease or condition of the brain. An "angiogenic disease or condition of the brain" is a disease or condition of the brain involving, exacerbated by, or caused by, angiogenesis. The method comprises administering to an animal in need thereof an amount of a steroid of formula I or IV or a pharmacologically-acceptable salt or ester thereof that is effective to inhibit the angiogenesis that is occurring in the brain.

Angiogenic diseases and conditions of the brain that can be treated according to the present invention include, but are not limited to, tumors, neovascularization due to brain damage (such as caused by traumatic or surgical injury of brain tissue or stroke).

Brain tumors that can be treated according to the present invention include, but are not limited to, any benign or cancerous tumor, including primary tumors and metastatic (secondary) tumors.

About half of all primary brain tumors are gliomas. Gliomas include astrocytomas (e.g., pilocytic astrocytomas, low-grade astrocytomas, anaplastic (high-grade) astrocytomas and glioblastomas multiforme), brain stem gliomas ependymomas, ganglioneuromas, juvenile pilocytic gliomas, mixed gliomas, oligodendrogliomas and optic nerve gliomas. Glioblastomas are the most common malignant brain tumors in adults and are probably the most resistant of all cancers to treatment.

Meningiomas account for about 27% of primary brain tumors, and most are benign. However, unlike benign tumors elsewhere, benign brain tumors can sometimes cause disability and may sometimes be life threatening. Meningiomas are often curable with surgery, but treatment according to the present invention can be used instead of or in addition to surgery.

Other primary brain tumors include chordomas, carniopharyngiomas, medulloblastomas, pineal tumors, pituitary adenomas, primitive neuroectodermal tumors, schwannomas and vascular tumors.

Metastatic brain tumors are tumors that have spread to the brain from another part of the body. The most common cancers that metastasize to the brain include breast, melanoma and lung cancers. Metastatic brain tumors are the most common form of brain tumor and considerably outnumber primary brain tumors.

The invention further provides a method of treating an inflammatory disease or condition of the eye. An "inflammatory disease or condition of the eye" is a disease or condition of the eye involving, exacerbated by, or caused by, inflammation. The method comprises administering to an animal in need thereof an amount of a steroid of formula I, IV or V or a pharmacologically-acceptable salt or ester thereof that is effective to inhibit the inflammation that is occurring in the eye.

Inflammatory diseases and conditions of the eye that can be treated according to the present invention include, but are not limited to, uveitis, scleritis, keratitis, retinitis, iritis, uveoretinitis, uveoscleritis, conjunctivitis, Mooren's ulcer and inflammatory ocular manifestations in allergies and in arthritic, rheumatic and connective tissue diseases (see, e.g., Bucknall, *Rheumatology*, 44(10):1207-1209 (2005).

The invention also provides a method of treating an inflammatory disease or condition of the brain. An "inflammatory disease or condition of the brain" is a disease or condition of the brain involving, exacerbated by, or caused by, inflammation. The method comprises administering to an animal in need thereof an amount of a steroid of formula I, IV or V or a pharmacologically-acceptable salt or ester thereof that is effective to inhibit the inflammation that is occurring in the brain.

Inflammatory diseases and conditions of the brain that can be treated according to the present invention include, but are not limited to, abscesses (including abscesses caused by bacterial, fungal and parasitic infections), meningitis (including bacterial meningitis, tuberculosis and sarcoidosis), encephalitis (including *Herpes simplex* encephalitis, Eastern and Western equine encephalitis, St. Louis encephalitis, California virus encephalitis, Lyme disease and post-infectious encephalitis), vasculitis, autism and neurodegenerative diseases.

Neurodegenerative diseases that can be treated according to the present invention include, but are not limited to, Alzheimer's disease, amyotrophic lateral sclerosis, Huntington's chorea, multiple sclerosis, Parkinson's disease and senile dementia.

"Treat," "treating" or "treatment" is used herein to mean to reduce (wholly or partially) the symptoms, duration or severity of a disease or condition, including curing the disease, or to prevent the disease or condition.

"Inhibit" or "inhibiting" is used herein to mean to reduce (wholly or partially) or to prevent.

"Angiogenesis" means the development of new blood vessels. "Angiogenesis" is also used herein to mean the same as, or to include, neovascularization, vascularization, arterialization and vasculogenesis.

As noted above, the steroids that can be used in the practice of the present invention are those compounds of formulas I, IV and V shown below and pharmacologically acceptable salts and esters thereof.

Formula I is:

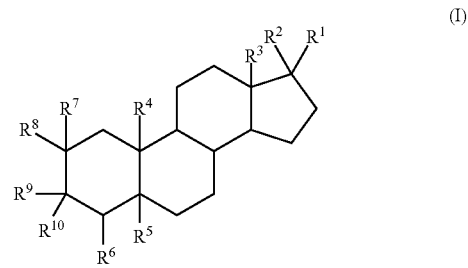

In Formula I:

$R^1$ is an alkyl group having from 1 to 6 carbon atoms, an alkenyl group having from 2 to 6 carbon atoms or an alkynyl group having from 2 to 6 carbon atoms;

$R^2$ is hydroxyl, an alkoxy group having from 1 to 6 carbon atoms, an alkanoyloxy group having from 1 to 7 carbon atoms, a group of formula (II) or a group of formula (III):

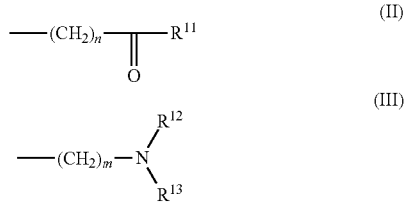

(II)

(III)

wherein $R^{11}$ is hydrogen, an alkyl group having from 1 to 6 carbon atoms, a hydroxyl group, an alkoxy group having from 1 to 6 carbon atoms or a group of formula —$N(R^{14})_2$ wherein each group $R^{14}$ is the same or different and is hydrogen or an alkyl group having from 1 to 6 carbon atoms, each of $R^{12}$ and $R^{13}$ is the same or different and is hydrogen or an alkyl group having from 1 to 6 carbon atoms, and m and n are the same or different and each is 0 or an integer of from 1 to 4;

each of $R^3$ and $R^4$ is the same or different and is hydrogen or an alkyl group having from 1 to 6 carbon atoms;

each of $R^5$ and $R^6$ is the same or different and is hydrogen or an alkyl group having from 1 to 6 carbon atoms or $R^5$ and $R^6$ together represent a single bond; and $R^7$, $R^8$, $R^9$ and $R^{10}$ together with the carbon atoms to which they are attached represent a 5- to 9-membered heterocyclic group, said 5- to 9-membered heterocyclic group optionally being substituted with from 1 to 7 substituents (said substituents are the same or different and are selected from substituent group α defined below).

Substituent group α is a group consisting of a halogen atom, a hydroxyl group, a cyano group, an amino group, an alkyl group having from 1 to 6 carbon atoms, an alkoxy group having from 1 to 6 carbon atoms, an alkylthio group having from 1 to 6 carbon atoms, an alkylsulfinyl group having from 1 to 6 carbon atoms, an alkylsulfonyl group having from 1 to 6 carbon atoms, a phenyl group and a group of formula —$N(R^{16})_2$ wherein each group $R^{16}$ is the same or different and is hydrogen or an alkyl group having from 1 to 6 carbon atoms.

Where $R^7$, $R^8$, $R^9$ and $R^{10}$ together with the carbon atoms to which they are attached represent an optionally substituted 5- to 9-membered heterocyclic group, said heterocyclic group is a 5- to 9-membered heterocyclic group containing from 1 to 4 atoms selected from a group consisting of a nitrogen atom, an oxygen atom and a sulfur atom and may be, for example, an unsaturated heterocyclic group such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyranyl group, a pyridyl group, a pyridazinyl group, a pyrimidinyl group, a pyrazinyl group, an azepinyl group, an azocinyl group or an azoninyl group; or a group wherein the unsaturated heterocyclic groups described above are partially or completely reduced, such as a morpholinyl group, a thiomorpholinyl group, a pyrrolidinyl group, a pyrrolinyl group, a imidazolidinyl group, a imidazolinyl group, a pyrazolidinyl group, a pyrazolinyl group, a piperidyl group, a piperazinyl group, a perhydroazepinyl group, a perhydroazocinyl group or a perhydroazoninyl group; preferably it is a 5- to 7-membered heterocyclic group containing one or more nitrogen atom and optionally containing an oxygen atom and/or a sulfur atom, which is, for example, an unsaturated heterocyclic group such as a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyridyl group, a pyridazinyl group, a pyrimidinyl group or a pyrazinyl group; or a group wherein this unsaturated heterocyclic group is partially or completely reduced, such as a morpholinyl group, a thiomorpholinyl group, a pyrrolidinyl group, a pyrrolinyl group, a imidazolidinyl group, a imidazolinyl group, a pyrazolidinyl group, a pyrazolinyl group, a piperidyl group or a piperazinyl group; and more preferably it is an isoxazolyl group or a pyrazolyl group for $R^7$, $R^8$, $R^9$ and $R^{10}$ together with the carbon atoms to which they are attached.

Formula IV is:

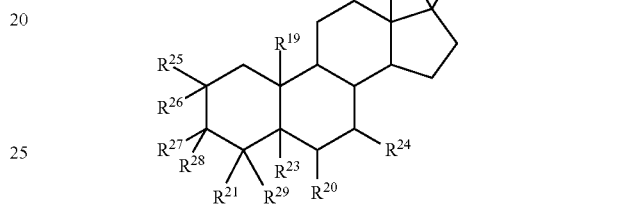

(IV)

In Formula IV:

$R^{18}$, $R^{19}$ and $R^{21}$ are the same or different and each is hydrogen or an alkyl group having from 1 to 6 carbon atoms;

$R^{17}$ is hydrogen, an alkyl group having from 1 to 6 carbon atoms or an alkenyl group having from 2 to 6 carbon atoms, $R^{22}$ is hydroxyl, an alkoxy group having from 1 to 6 carbon atoms, an alkanoyloxy group having from 1 to 7 carbon atoms, a group of formula (II) as defined above for formula (I) or a group of formula (III) as defined above for formula (I), or $R^{17}$ and $R^{22}$ together represent an oxo group, an ethylenedioxy group or a propylenedioxy group;

each of $R^{20}$ and $R^{24}$ is the same or different and is hydrogen or an alkyl group having from 1 to 6 carbon atoms or $R^{20}$ and $R^{24}$ together represent a single bond;

each of $R^{23}$ and $R^{29}$ is the same or different and is hydrogen or an alkyl group having from 1 to 6 carbon atoms or $R^{23}$ and $R^{29}$ together represent an epoxy linkage;

each of $R^{25}$, $R^{26}$, $R^{27}$ and $R^{28}$ is the same or different and is hydrogen, an alkyl group having from 1 to 6 carbon atoms, a cyano group, a hydroxyl group, an alkoxy group having from 1 to 6 carbon atoms or a group of formula —$N(R^{30})_2$ wherein each group $R^{30}$ is the same or different and is hydrogen or an alkyl group having from 1 to 6 carbon atoms, or $R^{25}$ and $R^{26}$ and/or $R^{27}$ and $R^{28}$ together with the carbon atom to which they are attached represent a carbonyl group, or $R^{25}$, $R^{26}$, $R^{27}$ and $R^{28}$ together with the carbon atoms to which they are attached represent a 5- to 9-membered heterocyclic group, said 5- to 9-membered heterocyclic group optionally being substituted with from 1 to 7 substituents (said substituents are the same or different and are selected from substituent group α defined above).

Where $R^{25}$, $R^{26}$, $R^{27}$ and $R^{28}$ together with the carbon atoms to which they are attached represent an optionally substituted 5- to 9-membered heterocyclic group, said heterocyclic group is a 5- to 9-membered heterocyclic group containing from 1 to 4 atoms selected from a group consisting of a nitrogen atom, an oxygen atom and a sulfur atom and may be, for example, an unsaturated heterocyclic group such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyranyl group, a pyridyl group, a pyridazinyl group, a pyrimidinyl group, a pyrazinyl group, an azepinyl group, an azocinyl group or an azoninyl group; or a group wherein the unsaturated heterocyclic groups described above are partially or completely reduced, such as a morpholinyl group, a thiomorpholinyl group, a pyrrolidinyl group, a pyrrolinyl group, a imidazolidinyl group, a imidazolinyl group, a pyrazolidinyl group, a pyrazolinyl group, a piperidyl group, a piperazinyl group, a perhydroazepinyl group, a perhydroazocinyl group or a perhydroazoninyl group; preferably it is a 5- to 7-membered heterocyclic group containing one or more nitrogen atom and optionally containing an oxygen atom and/or a sulfur atom, which is, for example, an unsaturated heterocyclic group such as a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyridyl group, a pyridazinyl group, a pyrimidinyl group or a pyrazinyl group; or a group wherein this unsaturated heterocyclic group is partially or completely reduced, such as a morpholinyl group, a thiomorpholinyl group, a pyrrolidinyl group, a pyrrolinyl group, a imidazolidinyl group, a imidazolinyl group, a pyrazolidinyl group, a pyrazolinyl group, a piperidyl group or a piperazinyl group; and more preferably it is an isoxazolyl group for $R^{25}$, $R^{26}$, $R^{27}$ and $R^{28}$ together with the carbon atoms to which they are attached.

Formula V is:

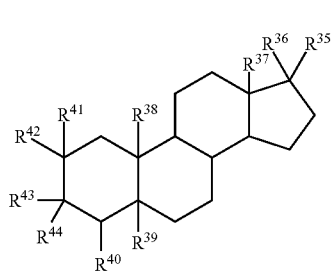

(V)

In Formula V:

$R^{35}$ is an alkyl group having from 1 to 6 carbon atoms, an alkenyl group having from 2 to 6 carbon atoms or an alkynyl group having from 2 to 6 carbon atoms;

$R^{36}$ is hydroxyl, an alkoxy group having from 1 to 6 carbon atoms, an alkanoyloxy group having from 1 to 7 carbon atoms, a group of formula (II) as defined above for formula (I) or a group of formula (III) as defined above for formula (I), or each of $R^{37}$ and $R^{38}$ is the same or different and is hydrogen or an alkyl group having from 1 to 6 carbon atoms;

each of $R^{39}$ and $R^{40}$ is the same or different and is hydrogen or an alkyl group having from 1 to 6 carbon atoms or $R^{39}$ and $R^{40}$ together represent a single bond;

each of $R^{41}$, $R^{42}$, $R^{43}$ and $R^{44}$ is the same or different and is hydrogen, an alkyl group having from 1 to 6 carbon atoms, a hydroxyl group, an alkoxy group having from 1 to 6 carbon atoms or a group of formula —N($R^{45}$)$_2$ wherein each group $R^{45}$ is the same or different and is hydrogen or an alkyl group having from 1 to 6 carbon atoms, or $R^{41}$ and $R^{42}$ and/or $R^{43}$ and $R^{44}$ together with the carbon atom to which they are attached represent a carbonyl group, or $R^{41}$, $R^{42}$, $R^{43}$ and $R^{44}$ together with the carbon atoms to which they are attached represent a 5- to 9-membered heterocyclic group, said 5- to 9-membered heterocyclic group optionally being substituted with from 1 to 7 substituents, which may be the same or different and are selected from substituent group α defined above.

Where $R^{41}$, $R^{42}$, $R^{43}$ and $R^{44}$ together with the carbon atoms to which they are attached represent an optionally substituted 5- to 9-membered heterocyclic group, said heterocyclic group is a 5- to 9-membered heterocyclic group containing from 1 to 4 atoms selected from a group consisting of a nitrogen atom, an oxygen atom and a sulfur atom and may be, for example, an unsaturated heterocyclic group such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyranyl group, a pyridyl group, a pyridazinyl group, a pyrimidinyl group, a pyrazinyl group, an azepinyl group, an azocinyl group or an azoninyl group; or a group wherein the unsaturated heterocyclic groups described above are partially or completely reduced, such as a morpholinyl group, a thiomorpholinyl group, a pyrrolidinyl group, a pyrrolinyl group, a imidazolidinyl group, a imidazolinyl group, a pyrazolidinyl group, a pyrazolinyl group, a piperidyl group, a piperazinyl group, a perhydroazepinyl group, a perhydroazocinyl group or a perhydroazoninyl group; preferably it is a 5- to 7-membered heterocyclic group containing one or more nitrogen atom and optionally containing an oxygen atom and/or a sulfur atom, which is, for example, an unsaturated heterocyclic group such as a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyridyl group, a pyridazinyl group, a pyrimidinyl group or a pyrazinyl group; or a group wherein this unsaturated heterocyclic group is partially or completely reduced, such as a morpholinyl group, a thiomorpholinyl group, a pyrrolidinyl group, a pyrrolinyl group, a imidazolidinyl group, a imidazolinyl group, a pyrazolidinyl group, a pyrazolinyl group, a piperidyl group or a piperazinyl group; and more preferably it is an isoxazolyl group or a $R^{44}$ pyrazolyl group for $R^{41}$, $R^{42}$, $R^{43}$ and $R^{44}$ together with the carbon atoms to which they are attached.

The alkyl group having from 1 to 6 carbon atoms is a straight or branched chain alkyl group having from 1 to 6 carbon atoms and may be, for example, a methyl group, an ethyl group, a propyl group, an isopropyl group, a butyl group, an isobutyl group, an s-butyl group, a t-butyl group, a pentyl group, an isopentyl group, a neopentyl group, a t-pentyl group, a 1-methylbutyl group, a hexyl group, a 1-methylpentyl group, a 2-methylpentyl group, a 3-methylpentyl group, a 1-ethylbutyl group or a 2-ethylbutyl group; preferably it is an alkyl group having from 1 to 4 carbon atoms such as a methyl group, an ethyl group, a propyl group, an isopropyl group, a butyl group, an isobutyl group, an s-butyl group or a t-butyl group; more preferably it is a methyl group, an ethyl group, a propyl group or an isopropyl group; and most preferably it is a methyl group.

The alkenyl group having from 2 to 6 carbon atoms is a straight or branched chain alkenyl group having from 2 to 6 carbon atoms and may be, for example, vinyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl and 5-hexenyl groups. Alkenyl groups having from 2 to 4 carbon atoms are preferred, and alkenyl groups having 2 or 3 carbon atoms are most preferred.

The alkynyl group having from 2 to 6 carbon atoms is a straight or branched chain alkynyl group having from 2 to 6 carbon atoms and may be, for example, ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl groups. Alkynyl groups having from 2 to 4 carbon atoms are preferred, and alkynyl groups having 2 or 3 carbon atoms are most preferred.

The alkanoyloxy group having from 1 to 7 carbon atoms is a carbonyloxy group (—COO—) the carbon atom of which is substituted with a hydrogen atom or an alkyl group having from 1 to 6 carbon atoms as described above and may be, for example, a formyloxy group, an acetyloxy group, a propionyloxy group, a butyryloxy group, an isobutyryloxy group, a pentanoyloxy group or a hexanoyloxy group; it is preferably an alkanoyloxy group having from 2 to 5 carbon atoms such as an acetyloxy group, a propionyloxy group, a butyryloxy group or an isobutyryloxy group; and more preferably it is an acetyloxy group.

The alkoxy group having from 1 to 6 carbon atoms is a hydroxy group in which the hydrogen atom is substituted with an alkyl group having from 1 to 6 carbon atoms as described above and may be, for example, a methoxy group, an ethoxy group, a n-propoxy group, an isopropoxy group, a n-butoxy group, an isobutoxy group, an s-butoxy group, a tert-butoxy group, an n-pentyloxy group, an isopentyloxy group, a 2-methylbutoxy group, a neopentyloxy group, an n-hexyloxy group, a 4-methylpentyloxy group, a 3-methylpentyloxy group, a 2-methylpentyloxy group, a 3,3-dimethylbutoxy group, a 2,2-dimethylbutoxy group, a 1,1-dimethylbutoxy group, a 1,2-dimethylbutoxy group, a 1,3-dimethylbutoxy group or a 2,3-dimethylbutoxy group; it is preferably an alkoxy group having from 1 to 4 carbon atoms such as a methoxy group, an ethoxy group, an n-propoxy group or an n-butoxy group; and more preferably it is a methoxy group.

The alkylthio group having from 1 to 6 carbon atoms is a mercapto group substituted with an alkyl group having from 1 to 6 carbon atoms as described above and may be, for example, a methylthio group, an ethylthio group, an n-propylthio group, an isopropylthio group, an n-butylthio group, an isobutylthio group, an s-butylthio group, a tert-butylthio group, an n-pentylthio group, an isopentylthio group, a 2-methylbutylthio group, a neopentylthio group, a 1-ethylpropylthio group, an n-hexylthio group, an isohexylthio group, a 4-methylpentylthio group, a 3-methylpentylthio group, a 2-methylpentylthio group, a 1-methylpentylthio group, a 3,3-dimethylbutylthio group, a 2,2-dimethylbutylthio group, a 1,1-dimethylbutylthio group, a 1,2-dimethylbutylthio group, a 1,3-dimethylbutylthio group, a 2,3-dimethylbutylthio group or a 2-ethylbutylthio group; it is preferably an alkylthio group having from 1 to 4 carbon atoms such as a methylthio group, an ethylthio group, an n-propylthio group or an n-butylthio group; and more preferably it is a methylthio group.

The alkylsulfinyl group having from 1 to 6 carbon atoms is a sulfinyl group (—SO—) which is substituted with an alkyl group having from 1 to 6 carbon atoms as described above and may be, for example, a methanesulfinyl group, an ethanesulfinyl group, an n-propanesulfinyl group, an isopropanesulfinyl group, an n-butanesulfinyl group, an isobutanesulfinyl group, an s-butanesulfinyl group, a tert-butanesulfinyl group, an n-pentanesulfinyl group, an isopentanesulfinyl group, a 2-methylbutanesulfinyl group, a neopentanesulfinyl group, an n-hexanesulfinyl group, a 4-methylpentanesulfinyl group, a 3-methylpentanesulfinyl group, a 2-methylpentanesulfinyl group, a 3,3-dimethylbutanesulfinyl group, a 2,2-dimethylbutanesulfinyl group, a 1,1-dimethylbutanesulfinyl group, a 1,2-dimethylbutanesulfinyl group, a 1,3-dimethylbutanesulfinyl group or a 2,3-dimethylbutanesulfinyl group; preferably it is an alkylsulfinyl group having from 1 to 4 carbon atoms such as a methanesulfinyl group, an ethanesulfinyl group, an n-propanesulfinyl group, an isopropanesulfinyl group or an n-butanesulfinyl group; and more preferably it is a methanesulfinyl group.

The alkylsulfonyl group having from 1 to 6 carbon atoms is a sulfonyl group (—SO$_2$—) substituted with an alkyl group having from 1 to 6 carbon atoms as described above and may be, for example, a methanesulfonyl group, an ethanesulfonyl group, an n-propanesulfonyl group, an isopropanesulfonyl group, an n-butanesulfonyl group, an isobutanesulfonyl group, an s-butanesulfonyl group, a tert-butanesulfonyl group, an n-pentanesulfonyl group, an isopentanesulfonyl group, a 2-methylbutanesulfonyl group, a neopentanesulfonyl group, an n-hexanesulfonyl group, a 4-methylpentanesulfonyl group, a 3-methylpentanesulfonyl group, a 2-methylpentanesulfonyl group, a 3,3-dimethylbutanesulfonyl group, a 2,2-dimethylbutanesulfonyl group, a 1,1-dimethylbutanesulfonyl group, a 1,2-dimethylbutanesulfonyl group, a 1,3-dimethylbutanesulfonyl group or a 2,3-dimethylbutanesulfonyl group; preferably it is an alkylsulfonyl group having from 1 to 4 carbon atoms such as a methanesulfonyl group, an ethanesulfonyl group, an n-propanesulfonyl group or an n-butanesulfonyl group; and more preferably it is a methanesulfonyl group.

Methods of making the steroids of formulas (I), (IV) and (V) are known in the art. See e.g., U.S. Pat. Nos. 3,135,743, 3,296,255 and GB 1,123,770 and 2,130,588. Also, danazol, trilostane and other compounds covered by formulas (I), (IV) and (V) are available commercially from, e.g., LKT Laboratories Inc., Mochida Pharmaceuticals, Sanofi Inc. and Sanofi Winthrop.

Where the compound of formula (I), (IV) or (V) of the present invention or a pharmacologically acceptable ester thereof has a basic group, the compound can be converted to a salt by reacting it with an acid, and in the case where the compound of formula (I), (IV) or (V) of the present invention or a pharmacologically acceptable ester thereof has an acidic group, the compound can be converted to a salt by reacting it with a base. The compounds of the present invention encompass such salts. Where said salts are to be used for a therapeutic use, they must be pharmacologically acceptable.

Preferred examples of the salts formed with a basic group present in the compound of formula (I), (IV) or (V) or a pharmacologically acceptable ester thereof include inorganic acid salts such as hydrohalogenated acid salts (e.g. hydrochlorides, hydrobromides and hydroiodides), nitrates, perchlorates, sulfates and phosphates; organic acid salts such as lower alkanesulfonates in which the lower alkyl moiety thereof is an alkyl group having from 1 to 6 carbon atoms as defined above (e.g. methanesulfonates, trifluoromethanesulfonates and ethanesulfonates), arylsulfonates in which the aryl moiety thereof is an aryl group having from 6 to 14 carbon atoms (e.g. benzenesulfonate or p-toluenesulfonate), acetates, malates, fumarates, succinates, citrates, ascorbates, tartrates, oxalates and maleates; and amino acid salts such as glycine salts, lysine salts, arginine salts, ornithine salts, glutamates and aspartates. Hydrohalogenated acid salts are particularly preferred.

Preferred example of the salts formed with an acidic group present in the compound of formula (I), (IV) or (V) or a pharmacologically acceptable ester thereof include metal salts such as alkali metal salts (e.g. sodium salts, potassium salts and lithium salts), alkali earth metal salts (e.g. calcium salts and magnesium salts), aluminium salts and iron salts; amine salts such as inorganic amine salts (e.g. ammonium salts) and organic amine salts (e.g. t-octylamine salts, dibenzylamine salts, morpholine salts, glucosamine salts, phenylglycinealkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts and tris(hydroxymethyl)aminomethane salts; and amino acid salts such as glycine salts, lysine salts, arginine salts, ornithine salts, glutamates and aspartates. Alkali metal salts are particularly preferred.

The compounds of formulas (I), (IV) and (V) of the present invention and pharmacologically acceptable salts and esters thereof of the present invention can sometimes take up water upon exposure to the atmosphere or when recrystallized to absorb water or to form a hydrate and such hydrates are also included within the scope of the present invention. Additionally, certain other solvents may be taken up by the compounds of the present invention to produce solvates, which also form a part of the present invention.

The compounds of formulas (I), (IV) and (V) of the present invention sometimes contain one or more asymmetric centres, and can therefore faun optical isomers (including diastereoisomers). For the compounds of the present invention, each of said isomers and mixture of said isomers are depicted by a single formula, i.e., the formula (I), (IV) or (V) respectively. Accordingly, the present invention covers both the individual isomers and mixtures thereof in any proportion, including racemic mixtures.

The present invention encompasses esters of the compounds of formulas (I), (IV) and (V). These esters are compounds of formulas (I), (IV) and (V) in which a hydroxyl group or a carboxy group of said compound of formula (I), (IV) or (V) is modified by the addition of a protecting group using conventional techniques well-known in the art (see, for example, "Protective Groups in Organic Synthesis, Second Edition, Theodora W. Greene and Peter G. M. Wuts, 1991, John Wiley & Sons, Inc.).

There is no particular restriction on the nature of this protecting group, provided that, where the ester is intended for therapeutic purposes, it must be pharmacologically acceptable, i.e. the protecting group must be capable of being removed by a metabolic process (e.g. hydrolysis) on administration of said compound to the body of a live mammal to give a compound of formula (I), (IV) or (V) or a salt thereof. In other words, the pharmacologically acceptable esters are pro-drugs of the compounds of formula (I), (IV) or (V) of the present invention.

Whether an ester of a compound of formula (I), (IV) or (V) of the present invention is pharmacologically acceptable can be easily determined. The compound under investigation is intravenously administered to an experimental animal such as a rat or mouse and the body fluids of the animal are thereafter studied. If a compound of formula (I), (IV) or (V) or a pharmacologically acceptable salt thereof can be detected in the body fluids, the compound under investigation is judged to be a pharmacologically acceptable ester.

The compounds of formula (I), (IV) or (V) of the present invention can be converted to an ester, examples of which include a compound of formula (I), (IV) or (V) in which a hydroxyl group present therein is esterified. The ester residue must be capable of being removed by a metabolic process (e.g. hydrolysis) in vivo in order for the esterified compound to be one which is pharmacologically acceptable. Preferred examples of such a protecting group include the following:

(i) 1-(acyloxy)lower alkyl groups, examples of which include:

1-(aliphatic acyloxy)lower alkyl groups which comprise an alkyl group having from 1 to 6 carbon atoms as defined above which is substituted with an alkylcarbonyloxy group having from 1 to 6 carbon atoms, examples of which include formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxy-propyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl groups, 1-(cycloalkylcarbonyloxy)lower alkyl groups which comprise an alkyl group having from 1 to 6 carbon atoms as defined above which is substituted with a cycloalkylcarbonyloxy group in which a carbonyloxy group is substituted with a cycloalkyl group having from 1 to 6 carbon atoms, examples of which include cyclopentylcarbonyloxymethyl, cyclohexylcarbonyloxy-methyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentyl-carbonyloxybutyl and 1-cyclohexylcarbonyloxybutyl groups, and 1-(aromatic acyloxy)lower alkyl groups which comprise an alkyl group having from 1 to 6 carbon atoms as defined above which is substituted with an arylcarbonyloxy group which comprises an oxygen atom which is substituted with an arylcarbonyl group, examples of which include benzoyloxymethyl groups;

(ii) substituted carbonyloxyalkyl groups, examples of which include:

(lower alkoxycarbonyloxy)alkyl groups which comprise an alkyl group having from 1 to 6 carbon atoms as defined above or a cycloalkyl group having from 1 to 6 carbon atoms which is substituted with a lower alkoxycatbonyloxy group which comprises a carbonyloxy group substituted with an alkoxy group having from 1 to 6 carbon atoms as defined above or a cycloalkoxy group having from 1 to 6 carbon atoms, examples of which include methoxycarbonyloxymethyl, ethoxycarbonyloxymethyl, propoxy-carbonyloxymethyl, isopropoxycarbonyloxymethyl, butoxycarbonyloxymethyl, isobutoxycarbonyloxymethyl, pentyloxycarbonyloxymethyl, hexyloxycarbonyloxy-methyl, cyclohexyloxycarbonyloxymethyl, cyclohexyloxycarbonyloxy(cyclohexyl)-methyl, 1-(methoxycarbonyloxy)ethyl, 1-(ethoxycarbonyloxy)ethyl, 1-(propoxy-carbonyloxy)ethyl, 1-(isopropoxycarbonyloxy)ethyl, 1-(butoxycarbonyloxy)ethyl, 1-(isobutoxycarbonyloxy)ethyl, 1-(t-butoxycarbonyloxy)ethyl, 1-(pentyloxycarbonyloxy)ethyl, 1-(hexyloxycarbonyloxy)ethyl, 1-(cyclopentyloxycarbonyloxy)-ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 1-(methoxy-carbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxy-carbonyloxy)propyl, 1-(pentyloxycarbonyloxy)propyl, 1-(hexyloxycarbonyloxy)-propyl, 1-(methoxycarbonyloxy)butyl, 1-(ethoxycarbonyloxy)butyl, 1-(propoxy-carbonyloxy)butyl, 1-(isopropoxycarbonyloxy)butyl, 1-(butoxycarbonyloxy)butyl, 1-(isobutoxycarbonyloxy)butyl, 1-(methoxycarbonyloxy)pentyl, 1-(ethoxy-carbonyloxy)pentyl, 1-(methoxycarbonyloxy)hexyl and 1-(ethoxycarbonyloxy)hexyl groups, and oxodioxolenylmethyl groups, which comprise a methyl group which is substituted with an oxodioxolenyl group which itself may optionally be substituted with a group selected from the group consisting of alkyl groups having from 1 to 6 carbon atoms as defined above and aryl groups having from 6 to 14 carbon atoms as defined above which may optionally be substituted with at least one alkyl group having from 1 to 6 carbon atoms as defined above, alkoxy group having from 1 to 6 carbon atoms as defined above or a halogen atom, examples of which include (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)-methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl groups;

(iii) phthalidyl groups which comprise a phthalidyl group which may optionally be substituted with a substituent selected from the group consisting of alkyl groups having from 1 to 6 carbon atoms as defined above and alkoxy groups having from 1 to 6 carbon atoms as defined above, examples of which include phthalidyl, dimethylphthalidyl and dimethoxyphthalidyl groups;

(iv) aliphatic acyl groups, examples of which include:
alkylcarbonyl groups having from 1 to 25 carbon atoms, examples of which include formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methyl-pentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosanoyl groups,
ester forming residues of a saturated or unsaturated $C_2$-$C_{10}$ aliphatic di-carboxylic acids such as a fumarate, a maleate, oxalate, malonate or succinate,
halogenated alkylcarbonyl groups having from 1 to 25 carbons in which the alkyl moiety thereof is substituted by at least one halogen atom, examples of which include chloroacetyl, dichloroacetyl, trichloroacetyl and trifluoroacetyl groups,
lower alkoxyalkylcarbonyl groups which comprise an alkylcarbonyl group having from 1 to 25 carbon atoms in which the alkyl moiety thereof is substituted with at least one $C_1$-$C_6$ alkoxy group as defined above, examples of said lower alkoxyalkylcarbonyl groups including methoxyacetyl groups, and
unsaturated alkylcarbonyl groups having from 1 to 25 carbon atoms, examples of which include acryloyl, propioloyl, methacryloyl, crotonoyl, isocrotonoyl and (E)-2-methyl-2-butenoyl groups;
of these, alkylcarbonyl groups having from 1 to 6 carbon atoms are preferred;

(v) aromatic acyl groups, examples of which include:
arylcarbonyl groups which comprise a carbonyl group which is substituted with an aryl group having from 6 to 14 carbon atoms as defined above, examples of which include benzoyl, α-naphthoyl and β-naphthoyl groups,
halogenated arylcarbonyl groups which comprise an arylcarbonyl group as defined above which is substituted with at least one halogen atom, examples of which include 2-bromobenzoyl, 4-chlorobenzoyl and 2,4,6-trifluorobenzoyl groups,
lower alkylated arylcarbonyl groups which comprise an arylcarbonyl group as defined above which is substituted with at least one alkyl group having from 1 to 6 carbon atoms as defined above, examples of which include 2,4,6-trimethyl-benzoyl and 4-toluoyl groups,
lower alkoxylated arylcarbonyl groups which comprise an arylcarbonyl group as defined above which is substituted with at least one alkoxy group having from 1 to 6 carbon atoms as defined above, examples of which include 4-anisoyl groups,
nitrated arylcarbonyl groups which comprise an arylcarbonyl group as defined above which is substituted with at least one nitro group, examples of which include 4-nitrobenzoyl and 2-nitrobenzoyl groups,
lower alkoxycarbonylated arylcarbonyl groups which comprise an arylcarbonyl group as defined above which is substituted with a carbonyl group which is itself substituted with an alkoxy group having from 1 to 6 carbon atoms as defined above, examples of which include 2-(methoxycarbonyl)benzoyl groups, and
arylated arylcarbonyl groups which comprise an arylcarbonyl group as defined above which is substituted with at least one aryl group having from 6 to 14 carbon atoms as defined above, examples of which include 4-phenylbenzoyl groups;

(vi) half-ester salt residues of succinic acid;
(vii) phosphate ester salt residues;
(viii) ester-forming residues of an amino acid such as glutamate and aspartate;
(ix) carbamoyl groups which may optionally be substituted with 1 or 2 alkyl groups having from 1 to 6 carbon atoms as defined above; and
(x) 1-(acyloxy)alkoxycarbonyl groups which comprise a lower alkoxycarbonyl group as defined above in which the lower alkoxy moiety is substituted with an aliphatic acyloxy group as defined above or an aromatic acyloxy group as defined above, examples of which include pivaloyloxymethyloxycarbonyl groups.

Of the above protecting groups which are capable of being removed by a metabolic process (e.g. hydrolysis) in vivo which are used to synthesise a compound of formula (I), (IV) or (V) in which a hydroxyl residue therein is modified, the $C_1$-$C_{25}$ alkylcarbonyl groups and substituted carbonyloxyalkyl groups are preferred.

Preferred compounds of formula (I) are compounds of formula (Ia) and pharmacologically acceptable salts and esters thereof:

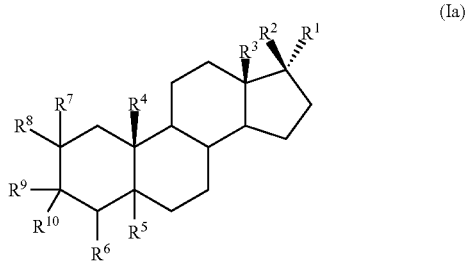

(Ia)

wherein $R^1$, $R^2$, $R^3$, $R^4$, $R^5$, $R^6$, $R^7$, $R^8$, $R^9$ and $R^{10}$ are as defined and exemplified above.

Of the compounds of formula (Ia) and pharmacologically acceptable salts and esters thereof, preferred are those wherein:

(i) $R^1$ is an alkyl group having from 1 to 4 carbon atoms, an alkenyl group having from 2 to 4 carbon atoms or an alkynyl group having from 2 to 4 carbon atoms;

(ii) $R^1$ is a methyl group or an ethynyl group;

(iii) $R^2$ is hydroxyl, an alkanoyloxy group having from 2 to 5 carbon atoms, a group of formula (II) wherein n is 0, 1 or 2, and $R^{11}$ is an alkyl group having from 1 to 4 carbon atoms, a hydroxyl group, an alkoxy group having from 1 to 4 carbon atoms or a group of formula —N($R^{14}$)$_2$ wherein each group $R^{14}$ is the same or different and is hydrogen or an alkyl group having from 1 to 4 carbon atoms or a group of formula (III) wherein m is 0, 1 or 2, and each of $R^{12}$ and $R^{13}$ is the same or different and is hydrogen or an alkyl group having from 1 to 4 carbon atoms;

(iv) $R^2$ is hydroxyl, an alkanoyloxy group having 2 or 3 carbon atoms, a group of formula (II) wherein n is 0 and $R^{11}$ is a methyl group, an ethyl group, a hydroxyl group, a methoxy group, an ethoxy group, an amino group, a methylamino group or a dimethylamino group, or a group of formula (III) wherein m is 0 or 1, and each of $R^{12}$ and $R^{13}$ is the same or different and is hydrogen, a methyl group or an ethyl group;

(v) $R^2$ is hydroxyl;

(vi) $R^3$ is hydrogen or an alkyl group having from 1 to 4 carbon atoms;

(vii) $R^3$ is a methyl group;

(viii) $R^4$ is hydrogen or an alkyl group having from 1 to 4 carbon atoms;

(ix) $R^4$ is a methyl group;

(x) $R^7$, $R^8$, $R^9$ and $R^{10}$ together with the carbon atoms to which they are attached represent a 5- to 7-membered heterocyclic group, said 5- to 7-membered heterocyclic group optionally being substituted with from 1 to 3 substituents (said substituents are the same or different and are selected from substituent group $\alpha^1$ defined below), and substituent group $\alpha^1$ is a group consisting of a halogen atom, a hydroxyl group, an amino group, an alkyl group having from 1 to 4 carbon atoms, an alkoxy group having from 1 to 4 carbon atoms, a phenyl group and a group of formula —N($R^{16a}$)$_2$ wherein each group $R^{16a}$ is the same or different and is hydrogen or an alkyl group having from 1 to 4 carbon atoms;

(xi) $R^7$, $R^8$, $R^9$ and $R^{10}$ together with the carbon atoms to which they are attached represent an isoxazolyl group; and (xii) each of $R^5$ and $R^6$ is a hydrogen atom or $R^5$ and $R^6$ together represent a single bond.

In each group of (i) to (ii), (iii) to (v), (vi) to (vii), (viii) to (ix) and (x) to (xi) compounds of formula (Ia) and pharmacologically acceptable salts and esters thereof having substituents falling within the larger numbered group are more preferred.

The compounds of formula (Ia) and pharmacologically acceptable salts and esters thereof which are given by an optional combination of $R^1$ selected from (i) to (ii), $R^2$ selected from (iii) to (v), $R^3$ selected from (vi) to (vii), $R^4$ selected from (viii) to (ix), $R^7$, $R^8$, $R^9$ and $R^{10}$ selected from (x) to (xi) and $R^5$ and $R^6$ selected from (xia) are also preferred.

Compounds of formula (Ia) and pharmacologically acceptable salts and esters thereof having the following combinations are particularly preferred:

(a) $R^1$=(i), $R^2$=(iii), $R^3$=(vi), $R^4$=(viii), $R^5$ and $R^6$=(xia), $R^7$, $R^8$, $R^9$ and $R^{10}$=(x);

(b) $R^1$=(ii), $R^2$=(iv), $R^3$=(vii), $R^4$=(ix), $R^5$ and $R^6$=(xia), $R^7$, $R^8$, $R^9$ and $R^{10}$=(x); and (c) $R^1$=(ii), $R^2$=(v), $R^3$=(vii), $R^4$=(ix), $R^5$ and $R^6$=(xia), $R^7$, $R^8$, $R^9$ and $R^{10}$=(xi).

The most preferred compounds of formula (Ia) and pharmacologically acceptable salts and esters thereof are danazol and stanozolol and pharmacologically acceptable salts and esters thereof:

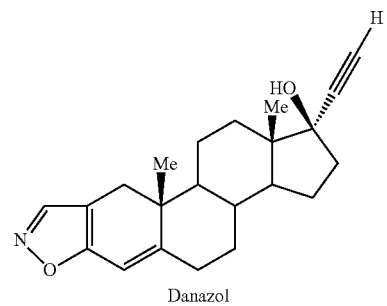

Danazol

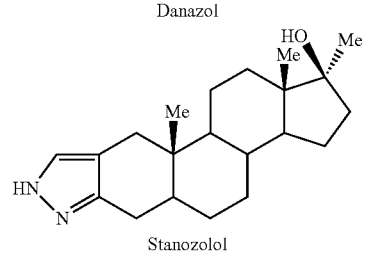

Stanozolol

Danazol and stanozolol are known synthetic steroid hormones having antiandrogen activity. Danazol (17α-pregna-2,4-dien-20-yno[2,3-d]-isoxazol-17β-ol) is a weak androgen that binds to numerous steroid hormone receptors and blocks the synthesis of estradiol, progesterone, testosterone and glucocorticoids; it is known for use as an oral agent employed in the treatment of endometriosis. Stanozolol (17-methyl-5α-androstano[3,2-c]pyrazol-17β-ol) is a synthetic testosterone analogue.

Computer modelling shows that danazol should cross the blood brain barrier (data not shown). As far as is known, it has not been reported prior to the present invention that danazol could do so.

Preferred compounds of formula (IV) are compounds of formula (IVa) and pharmacologically acceptable salts and esters thereof:

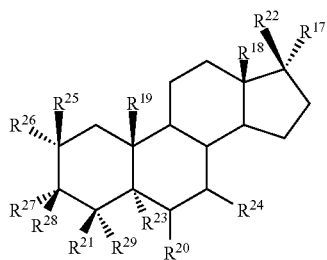
(IVa)

wherein $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ and $R^{29}$ are as defined and exemplified above.

Of the compounds of formula (IVa) and pharmacologically acceptable salts and esters thereof, preferred are those wherein:

(xii) each of $R^{18}$ and $R^{19}$ is the same or different and is hydrogen or an alkyl group having from 1 to 4 carbon atoms;
(xiii) each of $R^{18}$ and $R^{19}$ is a methyl group;
(xiv) each of $R^{20}$, $R^{21}$ and $R^{24}$ is the same or different and is a hydrogen atom or an alkyl group having from 1 to 4 carbon atoms or $R^{21}$ is a hydrogen atom and $R^{20}$ and $R^{24}$ together represent a single bond;
(xv) each of $R^{20}$, $R^{21}$ and $R^{24}$ is a hydrogen atom or $R^{21}$ is a hydrogen atom and $R^{20}$ and $R^{24}$ together represent a single bond;
(xvi) $R^{17}$ is hydrogen or an alkyl group having from 1 to 4 carbon atoms;
(xvii) $R^{17}$ is hydrogen;
(xviii) $R^{22}$ is hydroxyl, an alkanoyloxy group having from 2 to 5 carbon atoms, a group of formula (II) wherein n is 0, 1 or 2, and $R^{11}$ is an alkyl group having from 1 to 4 carbon atoms, a hydroxyl group, an alkoxy group having from 1 to 4 carbon atoms or a group of formula —N($R^{14}$)$_2$ wherein each group $R^{14}$ is the same or different and is hydrogen or an alkyl group having from 1 to 4 carbon atoms or a group of formula (III) wherein m is 0, 1 or 2, and each of $R^{12}$ and $R^{13}$ is the same or different and is hydrogen or an alkyl group having from 1 to 4 carbon atoms;
(xix) $R^{22}$ is hydroxyl, an alkanoyloxy group having 2 or 3 carbon atoms, a group of formula (II) wherein n is 0 and $R^{11}$ is a methyl group, an ethyl group, a hydroxyl group, a methoxy group, an ethoxy group, an amino group, a methylamino group or a dimethylamino group, or a group of formula (III) wherein m is 0 or 1, and each of $R^{12}$ and $R^{13}$ is the same or different and is hydrogen, a methyl group or an ethyl group;
(xx) $R^{17}$ and $R^{22}$ together represent an oxo group;
(xxi) each of $R^{23}$ and $R^{29}$ represents a hydrogen atom or $R^{23}$ and $R^{29}$ together represent an epoxy linkage;
(xxii) $R^{25}$ is hydrogen or an alkyl group having from 1 to 4 carbon atoms, $R^{26}$ is a cyano group and $R^{27}$ and $R^{28}$ together with the carbon atom to which they are attached represent a carbonyl group, or
$R^{25}$, $R^{26}$, $R^{27}$ and $R^{28}$ together with the carbon atoms to which they are attached represent a 5- to 7-membered heterocyclyl group, said 5- to 7-membered heterocyclyl group optionally being substituted with from 1 to 3 substituents (said substituents are the same or different and are selected from substituent group $\alpha^1$ defined above); and
(xxiii) $R^{25}$ is hydrogen, $R^{26}$ is a cyano group and $R^{27}$ and $R^{28}$ together with the carbon atom to which they are attached represent a carbonyl group, or
$R^{25}$, $R^{26}$, $R^{27}$ and $R^{28}$ together with the carbon atoms to which they are attached represent an isoxazolyl group.

In each group of (xii) to (xiii), (xiv) to (xv), (xvi) to (xvii), (xviii) to (xix) and (xxii) to (xxiii), compounds of formula (Na) and pharmacologically acceptable salts and esters thereof having substituents falling within the larger numbered group are more preferred.

The compounds of formula (IVa) and pharmacologically acceptable salts and esters thereof which are given by an optional combination of $R^{18}$ and $R^{19}$ selected from (xii) to (xiii), $R^{20}$, $R^{21}$ and $R^{24}$ selected from (xiv) to (xv), $R^{17}$ selected from (xvi), (xvii) and (xx), $R^{22}$ selected from (xviii) to (xx), $R^{23}$ and $R^{29}$ selected from (xxi) and $R^{25}$, $R^{26}$, $R^{27}$ and $R^{28}$ selected from (xxii) to (xxiii) are also preferred.

Compounds of formula (IVa) and pharmacologically acceptable salts and esters thereof having the following combinations are particularly preferred:

(d) $R^{18}$ and $R^{19}$=(xii), $R^{20}$, $R^{21}$ and $R^{24}$=(xiv), $R^{17}$=(xvi) and $R^{22}$=(xviii), $R^{23}$ and $R^{29}$=(xxi), and $R^{25}$, $R^{26}$, $R^{27}$ and $R^{28}$=(xxii);

(e) $R^{18}$ and $R^{19}$=(xiii), $R^{20}$, $R^{21}$ and $R^{24}$=(xv), $R^{17}$=(xvii) and $R^{22}$=(xix), $R^{23}$ and $R^{29}$=(xxi), and $R^{25}$, $R^{26}$, $R^{27}$ and $R^{28}$=(xxiii);

(f) $R^{18}$ and $R^{19}$=(xii), $R^{20}$, $R^{21}$ and $R^{24}$=(xiv), $R^{17}$ and $R^{22}$ together=(xx), $R^{23}$ and $R^{29}$=(xxi), and $R^{25}$, $R^{26}$, $R^{27}$ and $R^{28}$=(xxii); and (g) $R^{18}$ and $R^{19}$=(xiii), $R^{20}$, $R^{21}$ and $R^{24}$=(xv), $R^{17}$ and $R^{22}$ together=(xx), $R^{23}$ and $R^{29}$=(xxi), and $R^{25}$, $R^{26}$, $R^{27}$ and $R^{28}$=(xxiii).

The most preferred compounds of formula (IVa) and pharmacologically acceptable salts and esters thereof are trilostane, trilostane II, trliostane III, keto-trilostane and pharmacologically acceptable salts and esters thereof:

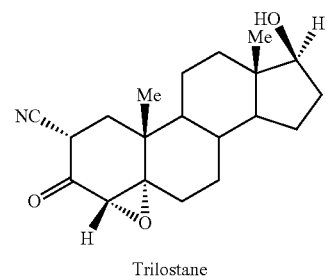

Trilostane

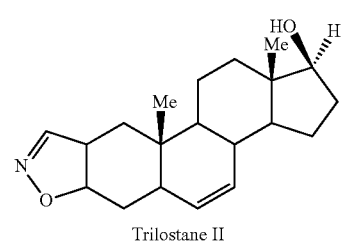

Trilostane II

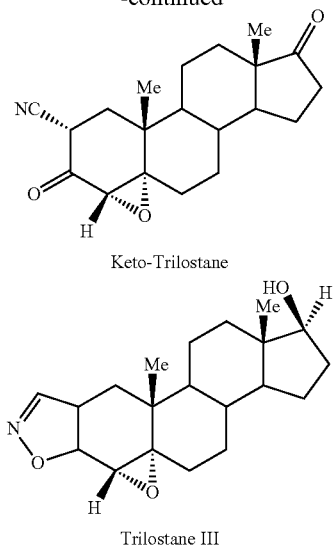

Keto-Trilostane

Trilostane III

Trilostane (2α-cyano-4α,5α-epoxyandrostan-17β-ol-3-one) and derivatives thereof are synthetic steroid hormones having activity in lowering the blood concentrations of glucocorticoids such as cortisol. Trilostane is known as an oral medication for the treatment of Cushing's Syndrome and advanced breast cancer and is described in UK Patent Nos. 1,123,770, 2,130,588 and 2,345,851, U.S. Pat. No. 3,296,295 and WO-A-02/080930, the contents of which are incorporated herein by reference thereto.

Computer modelling shows that trilostane should very readily cross the blood brain barrier (data not shown). As far as is known, it has not been reported prior to the present invention that trilostane could do so.

Preferred compounds of formula (V) are compounds of formula (Va) and pharmacologically acceptable salts and esters thereof:

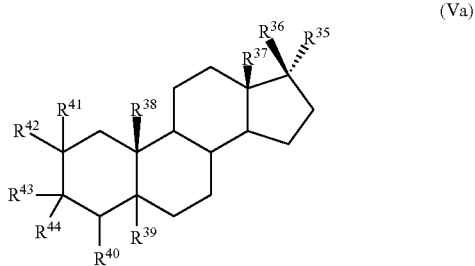

(Va)

wherein $R^{35}$, $R^{36}$, $R^{37}$, $R^{38}$, $R^{39}$, $R^{40}$, $R^{41}$, $R^{42}$, $R^{43}$ and $R^{44}$ are as defined and exemplified above.

Of these compounds of formula (Va) and pharmacologically acceptable salts and esters thereof, preferred are those wherein:
(i) $R^{35}$ is an alkyl group having from 1 to 4 carbon atoms, an alkenyl group having from 2 to 4 carbon atoms or an alkynyl group having from 2 to 4 carbon atoms;
(ii) $R^{35}$ is a methyl group or an ethynyl group;
(iii) $R^{36}$ is hydroxyl, an alkanoyloxy group having from 2 to 5 carbon atoms, a group of formula (II) wherein n is 0, 1 or 2, and $R^{11}$ is an alkyl group having from 1 to 4 carbon atoms, a hydroxyl group, an alkoxy group having from 1 to 4 carbon atoms or a group of formula —$N(R^{14})_2$ wherein each group $R^{14}$ is the same or different and is hydrogen or an alkyl group having from 1 to 4 carbon atoms or a group of formula (III) wherein m is 0, 1 or 2, and each of $R^{12}$ and $R^{13}$ is the same or different and is hydrogen or an alkyl group having from 1 to 4 carbon atoms;
(iv) $R^{36}$ is hydroxyl, an alkanoyloxy group having 2 or 3 carbon atoms, a group of formula (II) wherein n is 0 and $R^{11}$ is a methyl group, an ethyl group, a hydroxyl group, a methoxy group, an ethoxy group, an amino group, a methylamino group or a dimethylamino group, or a group of formula (III) wherein m is 0 or 1, and each of $R^{12}$ and $R^{13}$ is the same or different and is hydrogen, a methyl group or an ethyl group;
(v) $R^{36}$ is hydroxyl;
(vi) $R^{37}$ is hydrogen or an alkyl group having from 1 to 4 carbon atoms;
(vii) $R^{37}$ is a methyl group;
(viii) $R^{38}$ is hydrogen or an alkyl group having from 1 to 4 carbon atoms;
(ix) $R^{38}$ is a methyl group;
(x) each of $R^{41}$ and $R^{42}$ is a hydrogen atom and $R^{43}$ and $R^{44}$ together with the carbon atom to which they are attached represent a carbonyl group, or
$R^{41}$, $R^{42}$, $R^{43}$ and $R^{44}$ together with the carbon atoms to which they are attached represent a 5- to 7-membered heterocyclic group, said 5- to 7-membered heterocyclic group optionally being substituted with from 1 to 3 substituents (said substituents are the same or different and are selected from substituent group $\alpha^1$ defined below), and
substituent group $\alpha^1$ represents a group consisting of a halogen atom, a hydroxyl group, an amino group, an alkyl group having from 1 to 4 carbon atoms, an alkoxy group having from 1 to 4 carbon atoms, a phenyl group and a group of formula —$N(R^{16a})_2$ wherein each group $R^{16a}$ is the same or different and is hydrogen or an alkyl group having from 1 to 4 carbon atoms;
(xi) $R^{41}$, $R^{42}$, $R^{43}$ and $R^{44}$ together with the carbon atoms to which they are attached represent an isoxazolyl group; and
(xii) each of $R^{39}$ and $R^{40}$ is a hydrogen atom or $R^{39}$ and $R^{40}$ together represent a single bond.

In each group of (i) to (ii), (iii) to (v), (vi) to (vii), (viii) to (ix) and (x) to (xi) compounds of formula (Va) and pharmacologically acceptable salts and esters thereof having substituents falling within the larger numbered group are more preferred.

The compounds of formula (Va) and pharmacologically acceptable salts and esters thereof which are given by an optional combination of $R^{35}$ selected from (i) to (ii), $R^{36}$ selected from (iii) to (v), $R^{37}$ selected from (vi) to (vii), $R^{38}$ selected from (viii) to (ix), $R^{41}$, $R^{42}$, $R^{43}$ and $R^{44}$ selected from (x) to (xi) and $R^{39}$ and $R^{40}$ selected from (xia) are also preferred.

Compounds of formula (Va) and pharmacologically acceptable salts and esters thereof having the following combinations are particularly preferred:
(a) $R^{35}$=(i), $R^{36}$=(iii), $R^{37}$=(vi), $R^{38}$=(viii), $R^{39}$ and $R^{40}$=(xia), $R^{41}$, $R^{42}$, $R^{43}$ and $R^{44}$ (x);
(b) $R^{35}$=(ii), $R^{36}$=(iv), $R^{37}$=(vii), $R^{38}$=(ix), $R^{39}$ and $R^{40}$=(xia), $R^{41}$, $R^{42}$, $R^{43}$ and $R^{44}$=(x); and
(c) $R^{35}$=(ii), $R^{36}$=(v), $R^{37}$=(vii), $R^{38}$=(ix), $R^{39}$ and $R^{40}$=(xia), $R^{41}$, $R^{42}$, $R^{43}$ and $R^{44}$=(xi).

The most preferred compounds of formula (Va) and pharmacologically acceptable salts and esters thereof are ethisterone, danazol and stanozolol and pharmacologically acceptable salts and esters thereof:

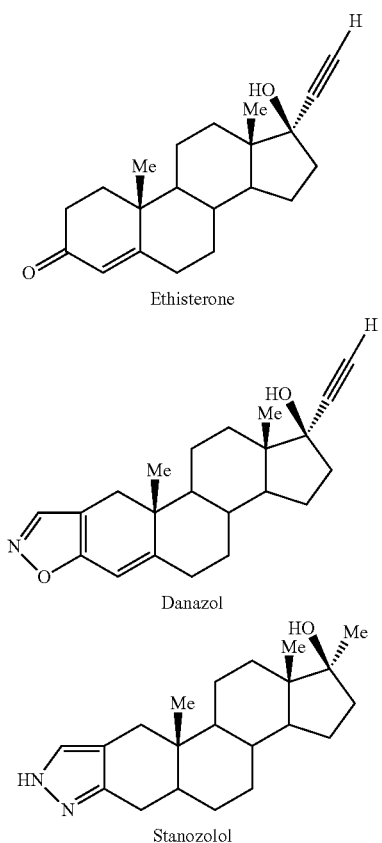

Ethisterone

Danazol

Stanozolol

Ethisterone is known a synthetic steroid hormone having antiandrogen activity. Ethisterone (17α-hydroxypregn-4-en-20-yn-3-one) is a progestogen that has been used in the past to treat menstrual disorders and as a component of combined oral contraceptives. Danazol and stanozolol were discussed above.

As noted above, a steroid of formula I or IV, or a pharmacologically-acceptable salt or ester thereof, can be used to treat an angiogenic disease or condition of the eye or brain. To do so, a steroid of formula I or IV, or a pharmacologically-acceptable salt or ester thereof, is administered to an animal in need of treatment. Preferably, the animal is a mammal, such as a rabbit, goat, dog, cat, horse or human. Most preferably, the animal is a human.

As also noted above, a steroid of formula I, IV or V, or a pharmacologically-acceptable salt or ester thereof, can be used to treat an inflammatory disease or condition of the eye or brain. To do so, a steroid of formula I, IV or V, or a pharmacologically-acceptable salt or ester thereof, is administered to an animal in need of treatment. Preferably, the animal is a mammal, such as a rabbit, goat, dog, cat, horse or human. Most preferably, the animal is a human.

Effective dosage forms, modes of administration and dosage amounts for the compounds of the invention may be determined empirically, and making such determinations is within the skill of the art. It is understood by those skilled in the art that the dosage amount will vary with the particular compound employed, the disease or condition to be treated, the severity of the disease or condition, the route(s) of administration, the rate of excretion of the compound, the duration of the treatment, the identify of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day. Administration of the compound should be continued until an acceptable response is achieved.

The compounds of the present invention (i.e., steroids of formulas (I), (IV) and (V) and pharmacologically-acceptable salts and esters thereof) may be administered to an animal patient for therapy by any suitable route of administration, including orally, nasally, parenterally (e.g., intravenously, intraperitoneally, subcutaneously or intramuscularly), transdermally, intraocularly and topically (including buccally and sublingually). The preferred routes of administration for treatment of diseases and conditions of the eye are orally, intraocularly and topically. Most preferred is topically. The preferred routes of administration for treatment of diseases and conditions of the brain are orally and parenterally. Most preferred is orally.

While it is possible for a compound of the present invention to be administered alone, it is preferable to administer the compound as a pharmaceutical formulation (composition). The pharmaceutical compositions of the invention comprise a compound or compounds of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., *Remington's Pharmaceutical Sciences*.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient (i.e., one or more steroids of the formulas set forth above and/or pharmacologically-acceptable salts and/or esters thereof) is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredient, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The invention also provides pharmaceutical products suitable for treatment of the eye. Such pharmaceutical products include pharmaceutical compositions, devices and implants (which may be compositions or devices).

Pharmaceutical formulations (compositions) for intraocular injection of a compound or compounds of the invention into the eyeball include solutions, emulsions, suspensions, particles, capsules, microspheres, liposomes, matrices, etc. See, e.g., U.S. Pat. No. 6,060,463, U.S. Patent Application Publication No. 2005/0101582, and PCT application WO 2004/043480, the complete disclosures of which are incorporated herein by reference. For instance, a pharmaceutical formulation for intraocular injection may comprise one or more compounds of the invention in combination with one or more pharmaceutically-acceptable sterile isotonic aqueous or non-aqueous solutions, suspensions or emulsions, which may contain antioxidants, buffers, suspending agents, thickening agents or viscosity-enhancing agents (such as a hyaluronic acid polymer). Examples of suitable aqueous and nonaqueous carriers include water, saline (preferably 0.9%), dextrose in water (preferably 5%), buffers, dimethylsulfoxide, alcohols and polyols (such as glycerol, propylene glycol, polyethylene glycol, and the like). These compositions may also contain adjuvants such as wetting agents and emulsifying agents and dispersing agents. In addition, prolonged absorption of the injectable pharmaceutical form may be brought about by the inclusion of agents which delay absorption such as polymers and gelatin. Injectable depot forms can be made by incorporating the drug into microcapsules or microspheres made of biodegradable polymers such as polylactide-polyglycolide. Examples of other biodegradable polymers include poly(orthoesters), poly(glycolic) acid, poly(lactic) acid, polycaprolactone and poly(anhydrides). Depot injectable formulations are also prepared by entrapping the drug in liposomes (composed of the usual ingredients, such as dipalmitoyl phosphatidylcholine) or microemulsions which are compatible with eye tissue. Depending on the ratio of drug to polymer or lipid, the nature of the particular polymer or lipid components, the type of liposome employed, and whether the microcapsules or microspheres are coated or uncoated, the rate of drug release from microcapsules, microspheres and liposomes can be controlled.

The compounds of the invention can also be administered surgically as an ocular implant. For instance, a reservoir container having a diffusible wall of polyvinyl alcohol or polyvinyl acetate and containing a compound or compounds of the invention can be implanted in or on the sclera. As another example, a compound or compounds of the invention can be incorporated into a polymeric matrix made of a polymer, such as polycaprolactone, poly(glycolic) acid, poly(lactic) acid, poly(anhydride), or a lipid, such as sebacic acid, and may be implanted on the sclera or in the eye. This is usually accomplished with the animal receiving a topical or local anesthetic and using a small incision made behind the cornea. The matrix is then inserted through the incision and sutured to the sclera.

A preferred embodiment of the invention is local topical administration of the compounds of the invention to the eye, and a particularly preferred embodiment of the invention is a topical pharmaceutical composition suitable for application to the eye. Topical pharmaceutical compositions suitable for application to the eye include solutions, suspensions, dispersions, drops, gels, hydrogels and ointments. See, e.g., U.S. Pat. No. 5,407,926 and PCT applications WO 2004/058289, WO 01/30337 and WO 01/68053, the complete disclosures of all of which are incorporated herein by reference.

Topical formulations suitable for application to the eye comprise one or more compounds of the invention in an aqueous or nonaqueous base. The topical formulations can also include absorption enhancers, permeation enhancers, thickening agents, viscosity enhancers, agents for adjusting and/or maintaining the pH, agents to adjust the osmotic pressure, preservatives, surfactants, buffers, salts (preferably sodium chloride), suspending agents, dispersing agents, solubilizing agents, stabilizers and/or tonicity agents. Topical formulations suitable for application to the eye will preferably comprise an absorption or permeation enhancer to promote absorption or permeation of the compound or compounds of the invention into the eye and/or a thickening agent or viscosity enhancer that is capable of increasing the residence time of a compound or compounds of the invention in the eye. See PCT applications WO 2004/058289, WO 01/30337 and WO 01/68053. Exemplary absorption/permeation enhancers include methysulfonylmethane, alone or in combination with dimethylsulfoxide, carboxylic acids and surfactants. Exemplary thickening agents and viscosity enhancers include dextrans, polyethylene glycols, polyvinylpyrrolidone, polysaccharide gels, Gelrite®, cellulosic polymers (such as hydroxypropyl methylcellulose), carboxyl-containing polymers (such as polymers or copolymers of acrylic acid), polyvinyl alcohol and hyaluronic acid or a salt thereof.

Liquid dosage forms (e.g., solutions, suspensions, dispersions and drops) suitable for treatment of the eye can be prepared, for example, by dissolving, dispersing, suspending, etc. a compound or compounds of the invention in a vehicle, such as, for example, water, saline, aqueous dextrose, glycerol, ethanol and the like, to form a solution, dispersion or suspension. If desired, the pharmaceutical formulation may also contain minor amounts of non-toxic auxiliary substances, such as wetting or emulsifying agents, pH buffering agents and the like, for example sodium acetate, sorbitan monolaurate, triethanolamine sodium acetate, triethanolamine oleate, etc.

Aqueous solutions and suspensions suitable for treatment of the eye can include, in addition to a compound or compounds of the invention, preservatives, surfactants, buffers, salts (preferably sodium chloride), tonicity agents and water. If suspensions are used, the particle sizes should be less than 10 μm to minimize eye irritation. If solutions or suspensions are used, the amount delivered to the eye should not exceed 50 μl to avoid excessive spillage from the eye.

Colloidal suspensions suitable for treatment of the eye are generally formed from microparticles (i.e., microspheres, nanospheres, microcapsules or nanocapsules, where microspheres and nanospheres are generally monolithic particles of a polymer matrix in which the formulation is trapped, adsorbed, or otherwise contained, while with microcapsules and nanocapsules the formulation is actually encapsulated). The upper limit for the size of these microparticles is about 5μ to about 10μ.

Ophthalmic ointments suitable for treatment of the eye include a compound or compounds of the invention in an appropriate base, such as mineral oil, liquid lanolin, white petrolatum, a combination of two or all three of the foregoing, or polyethylene-mineral oil gel. A preservative may optionally be included.

Ophthalmic gels suitable for treatment of the eye include a compound or compounds of the invention suspended in a hydrophilic base, such as Carpobol-940 or a combination of ethanol, water and propylene glycol (e.g., in a ratio of 40:40:20). A gelling agent, such as hydroxylethylcellulose, hydroxypropylcellulose, hydroxypropylmethylcellulose or ammoniated glycyrrhizinate, is used. A preservative and/or a tonicity agent may optionally be included.

Hydrogels suitable for treatment of the eye are formed by incorporation of a swellable, gel-forming polymer, such as those listed above as thickening agents or viscosity enhancers, except that a formulation referred to in the art as a "hydrogel" typically has a higher viscosity than a formulation referred to as a "thickened" solution or suspension. In contrast to such preformed hydrogels, a formulation may also be prepared so to form a hydrogel in situ following application to the eye. Such gels are liquid at room temperature but gel at higher temperatures (and thus are termed "thermoreversible" hydrogels), such as when placed in contact with body fluids. Biocompatible polymers that impart this property include acrylic acid polymers and copolymers, N-isopropylacrylamide derivatives and ABA block copolymers of ethylene oxide and propylene oxide (conventionally referred to as "poloxamers" and available under the Pluronic® tradename from BASF-Wayndotte).

Preferred dispersions are liposomal, in which case the formulation is enclosed within liposomes (microscopic vesicles composed of alternating aqueous compartments and lipid bilayers).

Eye drops can be formulated with an aqueous or nonaqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

The compounds of the invention can also be applied topically by means of drug-impregnated solid carrier that is inserted into the eye. Drug release is generally effected by dissolution or bioerosion of the polymer, osmosis, or combinations thereof. Several matrix-type delivery systems can be used. Such systems include hydrophilic soft contact lenses impregnated or soaked with the desired compound of the invention, as well as biodegradable or soluble devices that need not be removed after placement in the eye. These soluble ocular inserts can be composed of any degradable substance that can be tolerated by the eye and that is compatible with the compound of the invention that is to be administered. Such substances include, but are not limited to, poly(vinyl alcohol), polymers and copolymers of polyacrylamide, ethylacrylate and vinylpyrrolidone, as well as cross-linked polypeptides or polysaccharides, such as chitin.

Dosage forms for the other types of topical administration (i.e., not to the eye) or for transdermal administration of compounds of the invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required. The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane. Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Liquid sprays are conveniently delivered from pressurized packs. Typical of atomizers are the Mistometer (Wintrop) and Medihaler (Riker).

Nose drops may be formulated with an aqueous or non-aqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Additional objects, advantages and novel features of the present invention will become apparent to those skilled in the art by consideration of the following non-limiting examples.

EXAMPLES

Example 1

Trilostane III Effect on HUVEC Angiogenesis: Invasion Chamber

Purpose:
To examine the effect of trilostane III on fetal calf serum induced endothelial cells invasion through matrigel treated inserts.

Materials:
Passage 5 Human umbilical vein endothelial cells 7016 (HUVEC), Cambrex (Walkersville, Md.)
EGM-2 medium, Cambrex (Walkersville, Md.), supplemented to include 0.1% or 5% fetal calf serum
10 mM LY294002 and LY303511 in DMSO, CalBiochem
50 mM trilostane III in ethanol, Bowman Research, Newport, South Wales, UK (prepared as, for example, described in GB 1,123,770)
4 mM Calcein AM in DMSO, Sigma (St. Louis, Mo.)
Hepes buffered saline solution (HBSS), Cambrex (Walkersville, Md.)
BD Biocoat Marigel Invasion Chamber, BD Biosciences (San Jose, Calif.)
microplate fluorescence reader Protocol: in Short
1. Trypsinized HUVEC cells from flasks grown in Cambrex EGM-2 media to 70-80% confluence were washed two times with 37° C. EGM-2 with 0.1% FCS.
2. Cell suspensions containing 30,000 cells and compounds in EGM-2 0.1% FCS were added to the upper chamber of inserts.
3. EGM-2 containing 5% FCS was added to the bottom chamber and then incubated for 24 hours at 37° C. and 5% $CO_2$.
4. Non-invading cells were removed from the upper chamber with cotton swab and the inserts were washed two times with 37° C. HBSS.
5. Inserts were then placed in wells containing 10 µM Calcein AM in HBSS.
6. Following four hours at 37° C. and 5% $CO_2$, fluorescence was measured at 485 nm excitation and 595 nm emission.

Results and Observations:
Results are presented as mean fluorescent units (FU) in triplicate (n=3) with background fluorescence subtracted.

HUVEC 7016 cells were used for this experiment exhibiting 95% viability by trypan blue exclusion at time of seeding. To determine background invasion, nil inserts were included in triplicate that had EGM-2 with 0.1% FCS added to the bottom chamber. Without a chemotactic signal, these inserts will give a background invasion to compare the FCS and FCS plus compound wells. The results are as shown in Table 1 below and depicted graphically in FIG. 1.

TABLE 1

| Sample | Mean FU | std FU | SEM FU | p values vs 5% FCS |
|---|---|---|---|---|
| Nil | 9034 | 1688.2 | 974.687 | 0.024186 |
| 5% FCS | 12039.7 | 764.86 | 441.591 | |
| 50 μM Trilostane | 9101.33 | 540.28 | 311.928 | 0.002781 |
| 25 μM Trilostane | 11212.3 | 2748.7 | 1586.94 | 0.320938 |
| 50 μM LY 303511 | 12795.3 | 609.45 | 351.867 | 0.125899 |
| 50 μM LY 294002 | 9454.33 | 1877.9 | 1084.18 | 0.045893 |

Discussion and Conclusion:

The high dose of trilostane III dropped the levels back to background. LY294002, a known inhibitor of invasion, was included as a control and exhibited similar inhibition as trilostane. LY303511 is an inactive variant of the LY294002 and had no effect on invasion as expected. In conclusion, it would seem that trilostane III has an effect on endothelial cell invasion in certain individuals or at the appropriate time in the cell cycle.

Example 2

Trilostane III Effect on HUVEC Cell Proliferation

Figure 2:
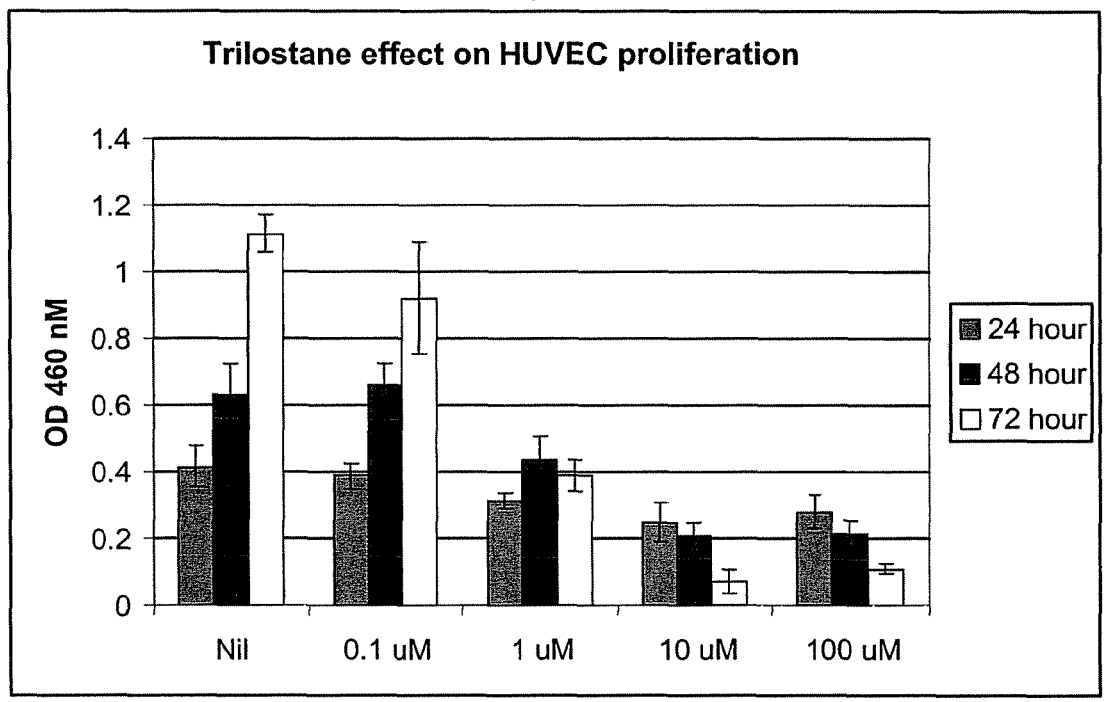
FIG. 2 shows the OD levels measured after incubation of HUVEC cells with trilostane III as a measure of its ability to prevent initial proliferation of endothelial cells.

Purpose:
To determine the effect trilostane III has on HUVEC cell proliferation.
Materials:
Passage 2 Human umbilical vein endothelial cells (HUVEC), Cambrex
EGM-2 medium supplemented to include 0.1% and 5% fetal calf serum, Cambrex
50 mM trilostane III in ethanol, Bowman Research, Newport, South Wales, UK (prepared as, for example, described in GB 1,123,770)
Hepes buffered saline solution (HBSS), Cambrex
Celltiter 96 Aqueous One reagent, Promega
Falcon 96 well tissue culture plates
Microplate fluorescence reader
Protocol:
1. HUVEC cells were plated in 96 well plates at 5,000 cells/cm$^2$ and incubated for 24 hours at 37° C. and 5% CO$_2$ in EGM-2 media.
2. Medium was aspirated and the cells were then washed two times with 37° C. HBSS.
3. EGM-2 containing 5% FCS with and without the compound (0.01 μM-200 μM trilostane III) was added to the wells and incubated for 24, 48, or 72 hours.
4. Cells were again washed to times with warm HBSS and then Celltiter reagent in EGM-2 with 0.1% FCS was added.
5. After 4 hours in culture the OD of each well was determine at 470 nm.
6. Repeat steps 4 and 5 for each time point.
Results and Observations:
Results are presented as mean OD of samples performed in triplicate (n=3) with mean blank OD subtracted. HUVEC 8750 cells were used for this experiment with 98% viability by trypan blue exclusion at time of seeding. Extra fetal calf serum (2% increased to 5%) was added to keep trilostane III in solution. The raw data are shown in Table 2 below and depicted graphically in FIG. 2.

TABLE 2

| Trilostane III | | | |
|---|---|---|---|
| Sample | 24 hour | 48 hour | 72 hour |
| Nil | 0.414 | 0.629333 | 1.1135 |
| 0.1 uM | 0.387333 | 0.656 | 0.918667 |
| 1 uM | 0.311 | 0.434667 | 0.387667 |
| 10 uM | 0.246667 | 0.203 | 0.072 |
| 100 uM | 0.278667 | 0.214667 | 0.108 |

| Trilostane III 24 hour results | | | | | |
|---|---|---|---|---|---|
| Sample | OD 1 | OD 2 | OD 3 | std | pvalue vs Nil |
| Nil | 0.345 | 0.457 | 0.44 | 0.060357 | |
| 0.1 uM | 0.362 | 0.368 | 0.432 | 0.038799 | 0.277404 |
| 1 uM | 0.284 | 0.328 | 0.321 | 0.023643 | 0.025631 |
| 10 uM | 0.18 | 0.267 | 0.293 | 0.059181 | 0.013283 |
| 100 uM | 0.235 | 0.334 | 0.267 | 0.050521 | 0.020409 |

| Trilostane III 48 hour results | | | | | |
|---|---|---|---|---|---|
| Sample | OD 1 | OD 2 | OD 3 | std | pvalue vs Nil |
| Nil | 0.521 | 0.666 | 0.701 | 0.095438 | |
| 0.1 uM | 0.575 | 0.698 | 0.695 | 0.070164 | 0.358232 |
| 1 uM | 0.358 | 0.489 | 0.457 | 0.068296 | 0.022665 |
| 10 uM | 0.159 | 0.208 | 0.242 | 0.041725 | 0.001045 |
| 100 uM | 0.17 | 0.23 | 0.244 | 0.039311 | 0.001121 |

| Trilostane III 72 hour results | | | | | |
|---|---|---|---|---|---|
| Sample | OD 1 | OD 2 | OD 3 | std | pvalue vs Nil |
| Nil | | 1.075 | 1.152 | 0.054447 | |
| 0.1 uM | 0.733 | 0.962 | 1.061 | 0.168239 | 0.113558 |
| 1 uM | 0.387 | 0.437 | 0.339 | 0.049003 | 0.000285 |
| 10 uM | 0.031 | 0.095 | 0.09 | 0.035595 | 5.8E−05 |
| 100 uM | 0.092 | 0.119 | 0.113 | 0.014177 | 3.09E−05 |

Discussion and Conclusion:

Trilostane III proved effective at inhibiting endothelial cell proliferation. Concentrations as low as 1 μM (at 24 hours), exhibited statistically relevant decreases in cell proliferation. Increasing the dose to 100 μM, inhibited cultures by 33, 67, and 90% at 24, 48, and 72 hours respectively. The initial seeding of 1,500 cells per well is not detectable by the celltiter assay. Cells must expand to detectable levels so 100% inhibition can be expected and would not infer cell toxicity. Viable cells were visible in all wells examined under the inverted microscope, even at the highest doses after 72 hours in culture. These results indicate that trilostane III may be an effective antiangiogenic compound, by interfering with the initial proliferation of endothelial cells.

Example 3

Trilostane III Effect on HUVEC Angiogenesis: Tube Formation

Purpose:
To examine the effect of trilostane III on the formation of tube-like structures by HUVEC cells in an extracellular matrix gel.

Materials:
    Passage 3 Human umbilical vein endothelial cells (HUVEC), Cambrex
    EGM-2 medium, Cambrex: supplemented to include 0.1% or 5% fetal calf serum
        10 mM LY294002 and LY303511 in DMSO, CalBiochem
        50 mM trilostane III in ethanol, Bowman Research, Newport, South Wales, UK (prepared as, for example, described in GB 1,123,770)
    BD Biocoat Angiogenesis system: tube formation assay, BD Biosciences
    Microscope with camera Protocol: in Short
1. Trypsinized HUVEC cells from flasks grown in Cambrex EGM-2 media to 70-80% confluence were washed two times with 37° C. EGM-2 with 0.1% FCS.
2. Cell suspensions containing 10,000 cells and compounds in both EGM-2 0.1% and 5% FCS were added per well then incubated for 18 hours at 37° C. and 5% $CO_2$.
3. Following incubation, tube formations were photographed under microscope.

Results and Observations:
    Passage 3 HUVEC 8750 cells were used for this experiment at 98% viability by trypan blue exclusion at time of seeding. Few cells were obtained for this experiment but did not seem to interfere with the development of tubes. Pictures of representative wells for the compound and controls are shown in FIG. 3.

Discussion and Conclusion:
    The final step of angiogenesis is the formation of new vascular structures. HUVEC cells when grown in gels consisting of extraceluller matrix proteins, will exhibit a "latticework" of vacuoles that mimic the inner lumen of the capillary. Addition of fetal calf serum, or other angiogenic substances, will enhance the length and definition of these structures. Dosing with 50 μM trilostane III led to a decrease in branching, vacuole formation, and increase in satellite cells. 50 μM LY294002, a PI3 kinase inhibitor known to interfere with tube formation, completely inhibited the development seen in the nil wells while the inactive form exhibited comparable tube formations to untreated cells. The inclusion of 5% fetal calf serum to the wells increased tube definition and vacuole formation. 50 μM trilostane III and 50 μm LY294002 treatment greatly reduced tube formation in the presence of fetal calf serum. The untreated cells are far more susceptible to the effects of the control compounds and trilostane III. In conclusion, trilostane III appears to prohibit tube formation of HUVEC cells.

Example 4

Danazol Effect on HUVEC Cell Proliferation

Protocol:
    Primary HUVEC and EGM-2 growth medium were obtained from Cambrex (Walkersville, Md.). The cells were passaged in medium supplemented with 2% fetal calf serum (FCS) in tissue culture flasks at 37° C. and 5% $CO_2$. Subculturing was performed using trypsin when 60-80% confluence was obtained as specified by the supplier.
    Cryopreserved ampoules of passage 2 HUVEC cells were thawed and plated in 96 well tissue culture plates at 5,000 cells/cm². A 50 mM stock solution of danazol was prepared in ethanol and the FCS in the medium was increased to 5% to keep danazol in solution. The cells were treated with medium containing final concentrations of danazol ranging from 0.1 to 100 μM in triplicates. 24, 48, and 72 hour incubations were performed and cell proliferation was determined utilizing Celltiter 96 $AQ_{ueous}$ One Solution Cell Proliferation assay from Promega (Madison, Wis.). In short, medium was aspirated from each well and the cells were washed with 200 μl Hepes buffered saline (HBSS) from Cambrex warmed to 37° C. 100 μl diluted celltiter solution (15 μl stock+85 μl EGM-2 containing 0.1% FCS) were added to each well and incubated for an additional 4 hours. Optical density was determined by microplate reader using a 530 nm filter after blank subtraction and data presented as OD±standard deviation. The final concentration of ethanol in the wells was less then 0.2% and had no effect on cell proliferation or viability.
    All data are presented as representative experiment done in triplicate. Differences between subsets were analyzed using student t-test in Microsoft Excel. P<0.05 was considered statistically significant.

Results, Observations and Discussion:
    Culturing primary HUVEC endothelial cells in the presence of danazol decreased the OD obtained from the Promega celltiter proliferation assay in a time and dose dependent fashion (FIG. 4). The celltiter assay is based on the reduction of the assay solution by dehydrogenase enzymes to a formazan dye that directly correlates to cell number. Danazol treatment at 24 hours seemed to be effective only at very high doses. Significant decreases (p value <0.05) in assay OD were seen at 10 μM or greater concentrations of danazol. The OD detected in the nil wells was 0.414±0.06 and treatment with 10 μM danazol decreased the OD to 0.288±0.037 while 100 μM to 0.162±0.017, equating to percent inhibitions of 30% and 65% respectively. At 48 hours, the inhibition observed was significant even at physiological levels or approximately 1 μM. The nil reading obtained after 48 hours in culture increased to 0.629±0.095 and was reduced to 0.378±0.037 by 1 μM, 0.241±0.012 by 10 μM, and 0.19±0.033 by 100 μM (or percent inhibitions of 40%, 61%, and 70% respectively). After 72 hours, all danazol treatments tested exhibited significant reduction in HUVEC proliferation. The OD obtained in nil wells was 1.113±0.054 and after 0.1 μM treatment fell to 0.798±0.037, 1 μM to 0.484±0.022, 10 μM to 0.229±0.016, and 100 μM to 0.156±0.018 (inhibitions of 28%, 57%, 80%, and 86% respectively). Examination of the OD obtained from all 100 μM danazol doses was consistent at all time points indicating a complete arrest of cell proliferation at this concentration. In summary, danazol exhibited strong inhibition of endothelial cell proliferation.

Example 5

Danazol Effect on HUVEC Angiogenesis: Tube Formation

Protocol:
    To investigate the formation of capillary-like structures by HUVEC cells, the Angiogenesis System Endothelial Cell Tube Formation Assay was purchased from BD Biosciences (San Jose, Calif.) and used according to the manufacturers protocol. In brief, 100,000 HUVEC cells were seeded onto rehydrated matrigel plugs in 96 well tissue culture plates in the presence of 5% FCS to induce tube formation. Danazol was added to final concentrations of 1 μM, 10 μM, or 100 μM and LY294002 was added at 100 μM. After 18 hours the wells were photographed using a Kodak DCS Pro SLR/N digital camera (Rochester, N.Y.) mounted on an inverted microscope. Ethanol treated wells were included to determine if the vehicle had any effects on cell differentiation.

Figure 5:
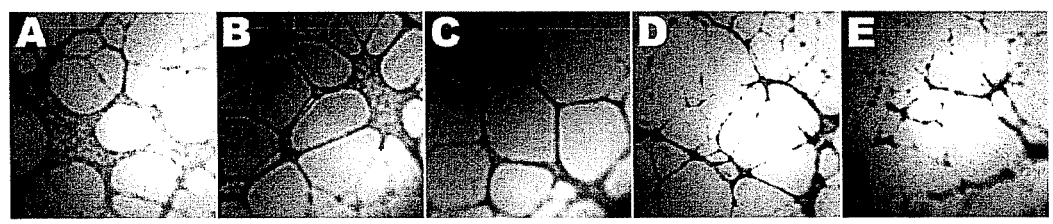
FIG. 5 shows photographs of HUVEC cells taken after incubation with danazol as a measure of its ability to prevent tube formation of endothelial cells. A=control; B=1 µM danazol, C=10 µM danazol, D=50 µM danazol and E=50 µM LY294002.

Results, Observations and Discussion:

To elucidate if danazol can prevent the formation of tube-like structures by HUVEC, 96 well plates containing matrigel plugs were used. Endothelial cells when cultured in the presence of angiogenic substances and supplied with an extracellular matrix scaffold will differentiate into structures loosely resembling capillary vessels. HUVEC cells grown with danazol exhibited fewer organized structures with thin and less defined interconnections than controls (see FIG. 5, in which A=control, B=1 µM danazol, C=10 µM danazol, D=50 µM danazol, and E=50 µM LY294002). Treatment with 50 µM danazol led to isolated colonies of HUVEC located in the plug with very few, thin connections or vessel lumen spaces. The effect of danazol was very similar to the positive control compound LY294002. To ensure that the vehicle used had no effect, wells were treated with ethanol at concentrations corresponding to the highest dose of danazol used and no effect on tube formation was observed (data not shown). Thes data indicate that danazol is an effective inhibitor of tube formation.

Example 6

Danazol Effect on HUVEC Angiogenesis: Invasion Chamber

Protocol:

BioCoat Matrigel Invasion Chambers were purchased from BD Biosciences (San Jose, Calif.). Inserts were rehydrated at 37° C. with 500 µl HBSS for 2 hours prior to use in humidified incubator. Trypsinized HUVEC cells were washed twice with warm EGM-2 containing 0.1% FCS and added to the upper chamber of the invasion insert at 100,000 cells in a total volume of 250 µl. Danazol and control compounds were added to the upper reservoir at final concentrations of 10 µM and 100 µM. 750 µl EGM-2 supplemented with 5% FCS was added to the bottom chamber to initiate invasion and the plates were incubated for 24 hours. Non-invasive cells were removed from the upper chamber with moistened cotton swabs and then the inserts were washed twice with HBSS. The inserts were then submerged in 10 µM calcein AM prepared in HBSS and incubated for 4 hours. Fluorescence was determined in a microplate reader at 485 nm excitation and 595 nm emission. LY294002 and the structurally similar but inactive compound LY303511 served as positive and negative controls respectively for this experiment.

Figure 6:
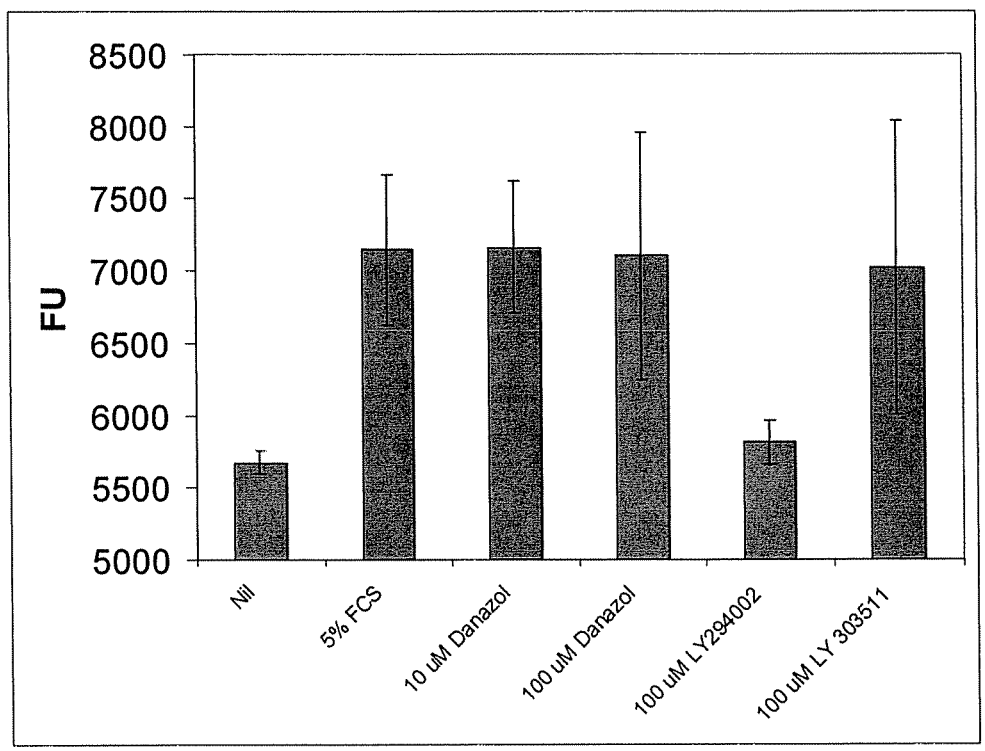
FIG. 6 shows the fluorescence measured after treatment of HUVEC cells with danazol as a measure of their ability to prevent endothelial cell invasion.

Results:

The results are presented in FIG. 6. All data is presented as representative experiment done in triplicate. Differences between subsets were analyzed using student t-test in Microsoft Excel. P<0.05 was considered statistically significant.

Porous, matrigel coated inserts were used to determine if danazol can interfere with the invasion or migration of endothelial cells (FIG. 6). In the system used for our study, a significant increase in cells was detected by fluorescent dye after the addition of FCS to the chamber opposite the endothelial cells (5674 FU±77 to 7143±516). Danazol at concentrations of 10 µM and 100 µM had no effect, while LY294002 showed almost complete attenuation of cell invasion (5814±153). These data indicate that factors present in the FCS induce the production of proteases that digest extracellular matrix by HUVEC cells followed by migration along a chemotactic gradient. Danazol has no apparent inhibitory effect on invasion and migration of HUVEC cells in this model.

What is claimed:

1. A method of treating an angiogenic disease or condition of the eye comprising administering to an animal in need thereof an effective amount of a trilostane compound selected from the group consisting of trilostane, trilostane II, trilostane III and keto-trilostane or a pharmacologically-acceptable salt or ester thereof and wherein the disease or condition of the eye is macular degeneration.

2. The method of claim 1 wherein administering comprises intraocular injection of the trilostane compound or a pharmacologically-acceptable salt or ester thereof into the eye.

3. The method of claim 1 wherein administering comprises topical administration of the trilostane compound or a pharmacologically-acceptable salt or ester thereof to the eye.

4. The method of claim 1 wherein administering comprises application of an ointment, a gel or a hydrogel comprising the trilostane compound or a pharmacologically-acceptable salt or ester thereof to the eye.

5. The method of claim 1 wherein administering comprises application of a solution comprising the trilostane compound or a pharmacologically-acceptable salt or ester thereof into the eye.

6. The method of claim 1 wherein administering comprises implantation of an ocular implant comprising the trilostane compound or a pharmacologically-acceptable salt or ester thereof into the eye.

7. The method of claim 1 wherein administering comprises insertion of a pharmaceutical device into the eye suitable for treatment of the eye.

8. The method of claim 7 wherein the device is a solid carrier impregnated with the trilostane compound or pharmacologically-acceptable salt or ester thereof.

9. The method of claim 8 wherein the device is a soft contact lens.

10. A method of treating an angiogenic condition of the eye comprising applying to an eye of an animal in need of such treatment, a topical pharmaceutical composition comprising a trilostane compound selected from the group consisting of trilostane, trilostane II, trilostane III and keto-trilostane or pharmacologically acceptable salts and esters thereof, wherein the composition is formulated for topical application to the eye and wherein the angiogenic condition of the eye is macular degeneration.

11. The method of claim 10, wherein the composition is a topical ophthalmic suspension.

12. The method of claim 11, wherein the ophthalmic suspension is a colloidal suspension.

13. The method of claim 10, wherein the composition is a topical ophthalmic solution.

14. The method of claim 13, wherein the ophthalmic solution comprises at least one of a dispersing agent, a solubilizing agent, a wetting agent, an emulsifying agent, a pH buffering agent, a preservative, a surfactant, a salt, a tonicity agent, and a suspending agent.

15. The method of claim 13, wherein the ophthalmic solution comprises a vehicle selected from the group consisting of water, saline, aqueous dextrose, glycerol, and ethanol.

16. The method of claim 10, wherein the composition is a topical ophthalmic gel.

17. The method of claim 16, wherein the ophthalmic gel comprises a hydrophilic base.

18. The method of claim 16, wherein the ophthalmic gel comprises Carpobol-940.

19. The method of claim 16, wherein the ophthalmic gel comprises a combination of ethanol, water and propylene glycol in a ratio of 40:40:20.

20. The method of claim 16, wherein the ophthalmic gel comprises at least one of a gelling agent, a preservative and a tonicity agent.

21. The method of claim 16, wherein the ophthalmic gel comprises a gelling agent selected from the group consisting of hydroxylethylcellulose, hydroxypropylcellulose, hydroxypropylmethylcellulose, and ammoniated glycyrrhizinate.

22. The method of claim 10, wherein the composition is a topical ophthalmic hydrogel.

23. The method of claim 22, wherein the hydrogel comprises a swellable, gel-forming polymer.

24. The method of claim 22, wherein the hydrogel is a thermoreversible hydrogel.

25. The method of claim 10, wherein the composition is a topical ophthalmic ointment.

26. The method of claim 25, wherein the ophthalmic ointment comprises a base selected from the group consisting of mineral oil, liquid lanolin, white petrolatum, polyethylene-mineral oil gel, or a combination thereof.

27. The method of claim 1 wherein the trilostane compound is trilostane III.

* * * * *